United States Patent [19]
Danby et al.

[11] Patent Number: 6,129,517
[45] Date of Patent: Oct. 10, 2000

[54] VOLUMETRIC INFUSION PUMP

[75] Inventors: Hal Danby, Chilton Sudbury; Thomas McGraghan, Colchester; Jon Plumb, Braintree; Alan Brundle, Halstead, all of United Kingdom; Martin Monaghan, Evanston; Svante Eric Myren, Crystal Lake, both of Ill.

[73] Assignee: Baxter International Inc, Deerfield, Ill.

[21] Appl. No.: 09/014,478

[22] Filed: Jan. 28, 1998

Related U.S. Application Data

[62] Division of application No. 08/672,367, Jun. 24, 1996, Pat. No. 5,842,841.

[30] Foreign Application Priority Data

Apr. 10, 1996 [GB] United Kingdom .................. 9607471

[51] Int. Cl.⁷ .................................................. F04B 49/00
[52] U.S. Cl. ............................................................ 417/63
[58] Field of Search ........................... 417/63, 474, 478, 417/479

[56] References Cited

U.S. PATENT DOCUMENTS

| | | | |
|---|---|---|---|
| 4,758,228 | 7/1988 | Williams | 604/153 |
| 4,781,548 | 11/1988 | Alderson et al. | 417/478 |
| 4,836,752 | 6/1989 | Burkett | 417/479 |
| 5,482,438 | 1/1996 | Anderson et al. | 417/474 |
| 5,567,120 | 10/1996 | Hungerford et al. | 417/63 |
| 5,938,413 | 8/1999 | Makino et al. | 417/474 |

FOREIGN PATENT DOCUMENTS 0 339 857  11/1989  European Pat. Off. ........ F04B 43/12

*Primary Examiner*—Charles G. Freay
*Attorney, Agent, or Firm*—Francis C. Kowalik

[57] ABSTRACT

A medical infusion pump is disclosed which has a tube present sensor that determines the position of the tube within a pumping body. The tube present sensor having a pivotable sensor arm with a blade which engages the tube. The pivotable sensor arm having a sensor flag which actuates an optical switch to signal that the sensor arm is in engagement with the tube. The sensor exchanges positional information with a pump controller to affect operation of the pump.

5 Claims, 31 Drawing Sheets

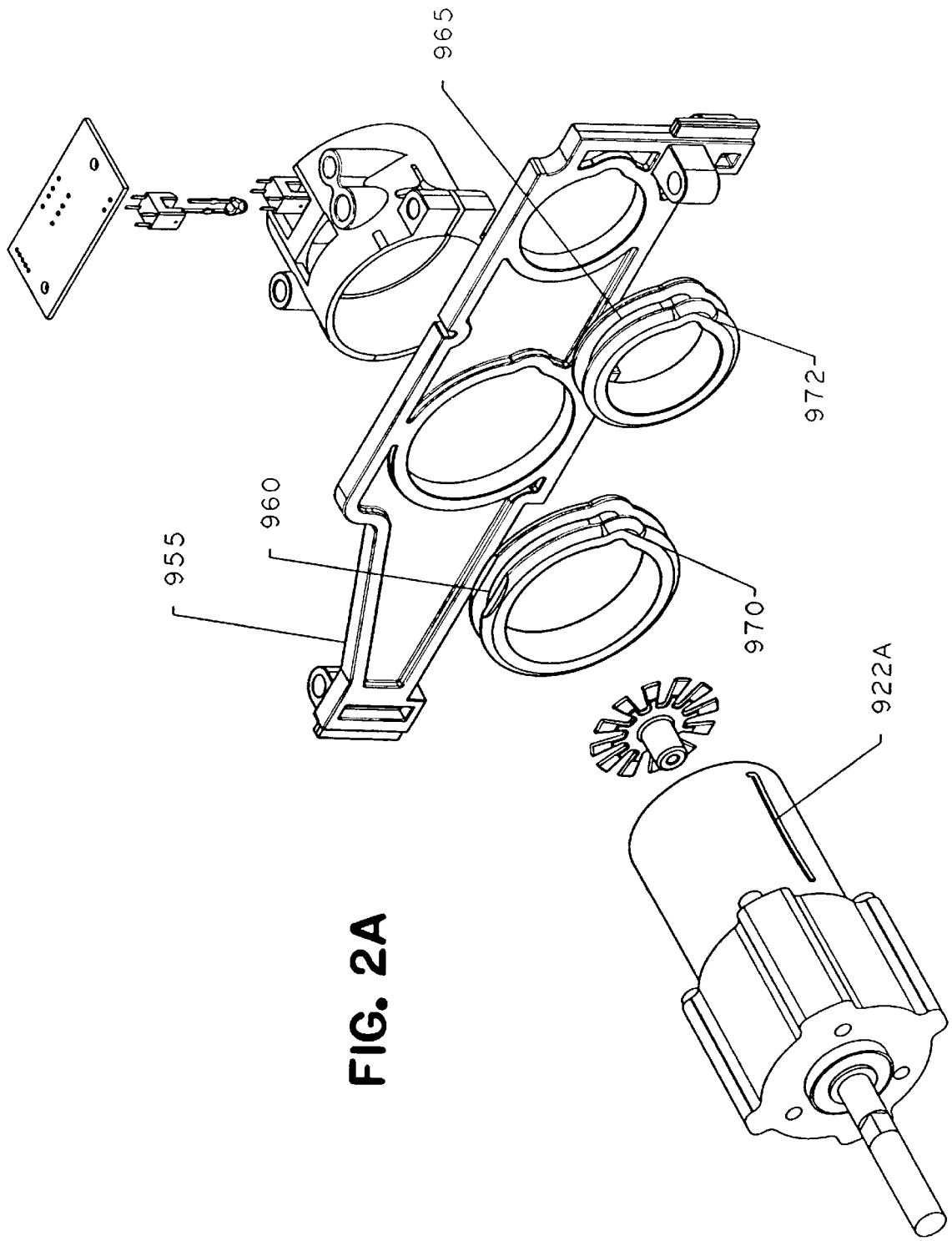

VOLUMETRIC INFUSION PUMP

This is a divisional of Application Ser. No. 08/672,367, filed on Jun. 24, 1996, now U.S. Pat. No. 5,842,841.

FIELD OF THE INVENTION

The instant invention relates to volumetric infusion pumps for parenteral delivery of fluids in a medical environment.

BACKGROUND OF THE INVENTION

Previous medical infusion pumps have comprehended a wide variety of methods for pumping fluids into a patient. The most common of these methods has been a peristaltic pump. In a peristaltic pump, a plurality of actuators or fingers serve to massage a parenteral fluid delivery tube in a substantially linear progression. The primary problem associated with peristaltic pumping technology is that the tube is repeatedly deformed in an identical manner, thereby over the course of time destroying the elastic recovery properties of the tube so that the tube maintains a compressed is aspect. This destruction of the elastic recovery properties of the tube results in the volumetric output of the pump changing markedly over time. Another common type of pump used in the volumetric delivery of medical fluids is commonly known as a cassette pump. Although cassette pumps do not display the fairly rapid degradation of performance as evidenced in a peristaltic pump, they require a fairly elaborate pump cassette to be integrated with the IV tube. This added expense of having to change a cassette along with an IV set every time an operator wishes to change the medicament delivered to the patient, significantly raises the cost of patient care. Additionally, as both peristaltic and cassette pumps, as well as other infusion devices present in the market, require a fairly elaborate knowledge of the specific pumping device to ensure that the IV set is loaded appropriately, generally medical infusion pumps were purely the purview of the nursing or medical staff in a hospital environment.

The necessity of manually loading a set into an IV pump is universal in the art. Generally when a standard IV set is used, in addition to the rapid degradation of accuracy mentioned above, great difficulty is encountered in correctly loading the set into those pumps presently in the art. The state of the art of loading technology as it relates to medical infusion pumps has progressed only to the state of enclosing the IV tube between a pumping device and a door or cover and adding progressively more elaborate sensors and alarms to assure that the tube is correctly loaded into the pump. Even so, loading errors occur with regularity requiring great efforts on the part of hospital staffs to ensure that critical errors are minimized.

The state of the art in infusion pumps also includes the requirement of manually assuring that a free-flow condition of medicament does not occur when an IV set is installed or removed from a pump. Although hospital staffs exercise great care and diligence in their attempts to assure that free-flow conditions do not occur, a demonstrable need for additional precautions directed to the prevention of a free-flow condition has been a continuous concern of healthcare workers.

U.S. Pat. No. 5,199,852 to Danby discloses a pumping arrangement including a squeezing device for deforming a length of pliant tubing first in one direction locally to reduce its volume, and in another direction tending to restore its original cross-section and on either side of the squeezing device, inlet and outlet valves which operate by occluding the tubing. The control of the valves is by a plurality of motors controlled by a micro-processor.

U.S. Pat. No. 5,151,091 to Danby et al. discloses a pumping device which alternately compresses and reforms a section of tubing.

U.S. Pat. No. 5,055,001 to Natwick et al. discloses an infusion pump with spring controlled valves designed to open at a specific predetermined pressure.

U.S. Pat. No. 3,489,097 to Gemeinhardt discloses a flexible tube pump having a unitary fixture operative to act as an inlet and outlet valve and a pumping body located therebetween, driven off an eccentric.

U.S. Pat. No. 2,922,379 to Schultz discloses a multi-line pump having an inlet and an outlet valve mechanism and a pumping body located therebetween wherein both the inlet valve mechanism and the outlet valve mechanism are driven from a single cam.

U.S. Pat. No. 3,359,910 to Latham discloses a cam driven pump having inlet and outlet valves driven from a single cam and a pump body driven by an eccentric co-rotating with the single cam.

U.S. Pat. No. 4,239,464 to Hein discloses a blood pump having an inlet and outlet plunger serving as valves and a displacement plunger located therebetween.

U.S. Pat. No. 5,364,242 to Olson describes a drug pump having at least one rotatable cam and a reciprocally mounted follower engaged with the cam in a tube which is compressed by the follower during rotation of the cam. In the embodiment disclosed there are three cams.

U.S. Pat. No. 5,131,816 to Brown et al. discloses a infusion pump containing a plurality of linear peristaltic pumps and includes a position encoder mounted on the pump motor shaft to determine when the shaft has reached the stop position in the pump cycle.

U.S. Pat. No. 4,950,245 to Brown et al. discloses a multiple pump which is individually controlled by a programmable controller within the pump.

U.S. Pat. No. 4,273,121 to Jassawalla discloses a medical infusion system including a cassette and a deformable diaphragm and inlet and outlet windows which are occludable to pump the fluid contained in the cassette.

U.S. Pat. No. 4,936,760 to Williams discloses a infusion pump adapted to use a special tube wherein the tube has diametrically opposed handles extending longitudinally thereon and wherein the handles are adapted to be gripped by pump actuators so as to deform the tube transversely by pulling or pushing on the handles.

U.S. Pat. No. 5,092,749 to Meijer discloses a drive mechanism for actuating the fingers of a peristaltic pump having a jointed arm pivotally attached at one end to a drive member and at the other end to a fixed point on the base of the pump and a rotary cam actuator mounted on the base to urge against the arm and reciprocate the drive member.

U.S. Pat. No. 4,850,817 to Nason et al. discloses a mechanical drive system for a medication infusion system comprising a cassette pump wherein inside the cassette a single cam drives the inlet and outlet valves as well as the pump mechanism.

U.S. Pat. No. 5,252,044 to Raines discloses a cassette pump.

U.S. Pat. No. 3,606,596 to Edwards discloses a drug dispensing pump.

U.S. Pat. No. 3,518,033 to Anderson discloses an extra-corporeal heart.

SUMMARY AND OBJECTS OF THE INVENTION

The instant invention provides for an infusion pump wherein the pump has a pumping body which consists of a v-shaped groove extending longitudinally along a pump assembly and has associated therewith a fixed, and a moveable jaw and a plurality of valves located at either end of the v-shaped groove or shuttle.

In operation, an operator such as a nurse or patient would commence infusion of a medicament by inserting a standard IV set tube into a tube loading orifice located on the front of the pump. Additionally, the operator would simultaneously insert a slide clamp which is associated with the tube into a appropriate slide clamp orifice located upstream, i.e. more toward the fluid source, of the tube loading orifice. The operator would then actuate a tube loading sequence in which a series of pawls and a moveable upper jaw would serve to seize the tube and draw it into a tubeway, part of which is comprised of the v-shaped groove and valves. As the loading cycle progresses the jaws and pawls close about the tube capturing the tube within the tubeway. Sequentially as the valves close to occlude the tube, the slide clamp would be moved to a position such that the slide clamp would no longer occlude the tube. Upon receipt of appropriate signals from associated electronics which would determine the pumping speed, allowable volume of air, temperature and pressure, the pump is actuated wherein fluid is drawn from the fluid source and expelled from the pump in a constant and metered amount.

Should the tube be misloaded into the tubeway or the tubeloading orifice, appropriate sensors would determine the existence of such a state and effect an alarm directed thereto.

At the end of the infusion, actuation by an operator would serve to automatically close the slide clamp and release the tube from the pump.

The pump comprehends a variety of sensors directed to improve the safety of the infusion of medicament in addition to the sensors recited previously which provide information on the state of the fluid passing through the pump, the pump comprehends a variety of sensors operative to provide information regarding the state of various mechanical sub-assemblies within the pump itself. Among the sensors are devices directed to providing positional location of the shuttle or v-shaped slot aforementioned, valve operation, slide clamp location, misload detection, and manual operation of the tubeloading assembly.

The sensors relating to the state of the fluid being passed through the pump have themselves been improved with regard to accuracy. This has been accomplished by the development of the method of making contact between the sensor and the tube such that the contact is normal to the tube and the tube is placed in contact with the various sensors in such a way that there is neither a volumetric nor a stress gradient across the tube.

Therefore, it is a primary object of the invention to provide for an infusion pump capable to delivering an accurate volume of medicament using a standard infusion set.

It is another object of the invention to provide an infusion pump having a pumping shuttle and valves associated therewith, wherein the pumping shuttle and valves are mechanically synchronized.

It is a further object of the invention to provide an infusion pump having greatly improved accuracy whereby the output of the pumping member is linearized over the course of a pumping cycle.

It is another object of the invention to provide for a plurality of valves in an infusion pump such that the valves are adapted to occlude an infusion set tube while having a shape adapted to promote the elastic recovery of the tube when the valve is released therefrom.

It is an additional object of the invention to provide an infusion pump having enhanced resistance to medication errors by providing for an automatically loaded slide clamp associated with the infusion set.

It is a further object of the invention to provide, in the aforementioned infusion pump having a resistance to medication errors, a slide clamp sensor operative to sense whether the slide clamp aforementioned is opened or closed.

It is an additional object of the invention to provide for a synchronized, automatic closure of the slide clamp at all times when a free flow of medicament is possible.

It is an additional primary object of the invention to provide for an infusion pump capable of automatically loading a standard IV set therein.

It is a further object of the invention to provide for an infusion pump capable of sensing an incorrectly automatically loaded IV set and further capable of releasing the set from the pump in a state operative to prevent free flow of medicament through the set.

It is another object of the invention to provide an auto-tubeloader assembly operative to automatically load and unload a standard IV set from an associated infusion pump.

It is an additional object of the invention to provide for a synchronization of the slide clamp state and the valve state such that when one of the valves is in an open state, the second of the valves is in a closed state and when both valves are in an open state, the slide clamp is in a closed state.

It is an additional object of the invention to provide for a partial cycle of the pumping member immediately subsequent to the tubeloading cycle, so as to ensure that the tube is properly seated in the pumping member aforementioned.

It is another object of the invention to provide a cam associated with the pumping member wherein the cam is operative to linearize the output of the pump.

It is a further object of the invention to provide for a variability of pumping speed over the course of a pumping cycle.

It is another object of the invention to provide a further linearization of pump output by varying the speed of the pumping member.

It is an additional object of the invention to provide a variability in pumping output over the course of an infusion by varying the speed of the pumping member.

It is a further object of the invention to provide for a hydrodynamic assistance in the elastic recovery of the tube during the fill portion of a pumping cycle.

It is another object of the invention to provide a pumping body having an aspect adapted to be assembled with other pumping bodies into a multiple channel pump having a single controller.

It is a further object of the invention to provide for a tubeloading assembly having pawls adapted to capture and restrain an IV tube within the pump.

It is another primary object of the invention to provide for a sensor housing and an actuation assembly associated with the housing adapted to place a sensor in substantially normal contact with the tube.

It is an additional object of the invention to provide for a sensor housing and an actuation assembly operative to place a sensor in contact with a tube such that the volumetric gradient across the tube beneath the sensor is essentially zero.

It is a further object of the invention to provide for a sensor housing and an actuation assembly operative to place a sensor in contact with a tube such that the stress gradient of the tube beneath the sensor is essentially zero.

It is another object of the invention to provide for a single datum body operative to fix the relative location of the various elements within the pump.

It is a further object of the invention to provide for a plurality of shafts associated with the single datum body and cooperative therewith to fix the relative location of the various elements of the pump.

It is an additional object of tie invention to provide a compact means for pumping a medicament.

It is a further object of the invention to provide for a fluid seal barrier operative to prevent fluid ingress to various electrical components of the pump.

It is another object of the invention to provide for a case having a geometry operative to enforce a downward orientation of the tube in those areas exterior to the pump.

It is a further object of the invention to provide for manual means for actuating the automatic tube loading feature.

These and other objects of the instant invention will become apparent in the detailed description of the preferred embodiment, claims and drawings appended hereto.

BRIEF DESCRIPTION OF THE DRAWINGS

FIG. 2A is an exploded view of the motor mounts and pump drive motor.

DETAILED DESCRIPTION OF THE PREFERRED EMBODIMENT

Figure 1:
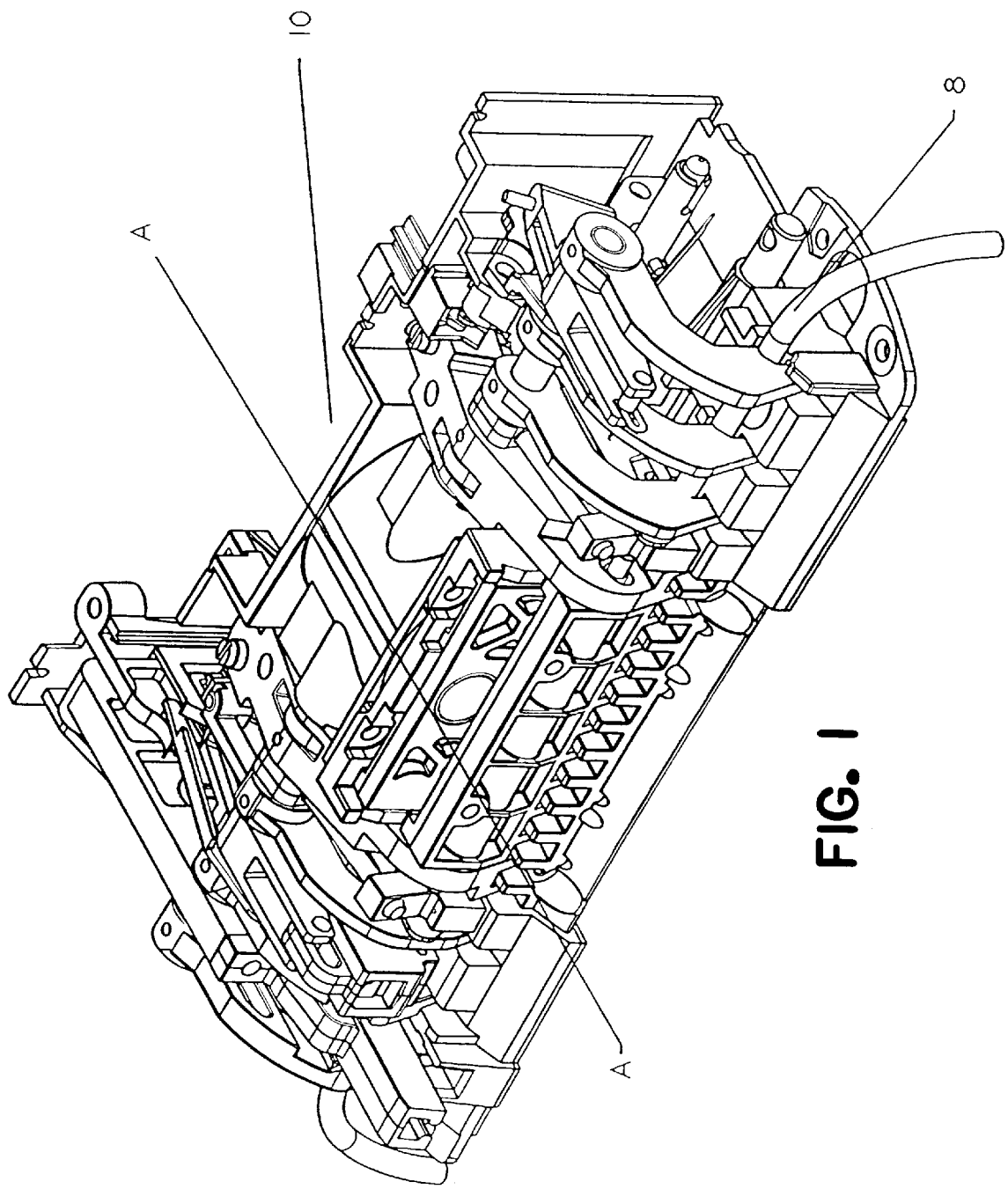
FIG. 1 is an isometric view of the complete pump assembly.

In the preferred embodiment of the instant invention, pump assembly 10 consists of a plurality of sub-assemblies as shown in FIG. 1, which perform various associated functions in concert with the pump sub-assembly 12.

The Pump Sub-assembly

Figure 2:
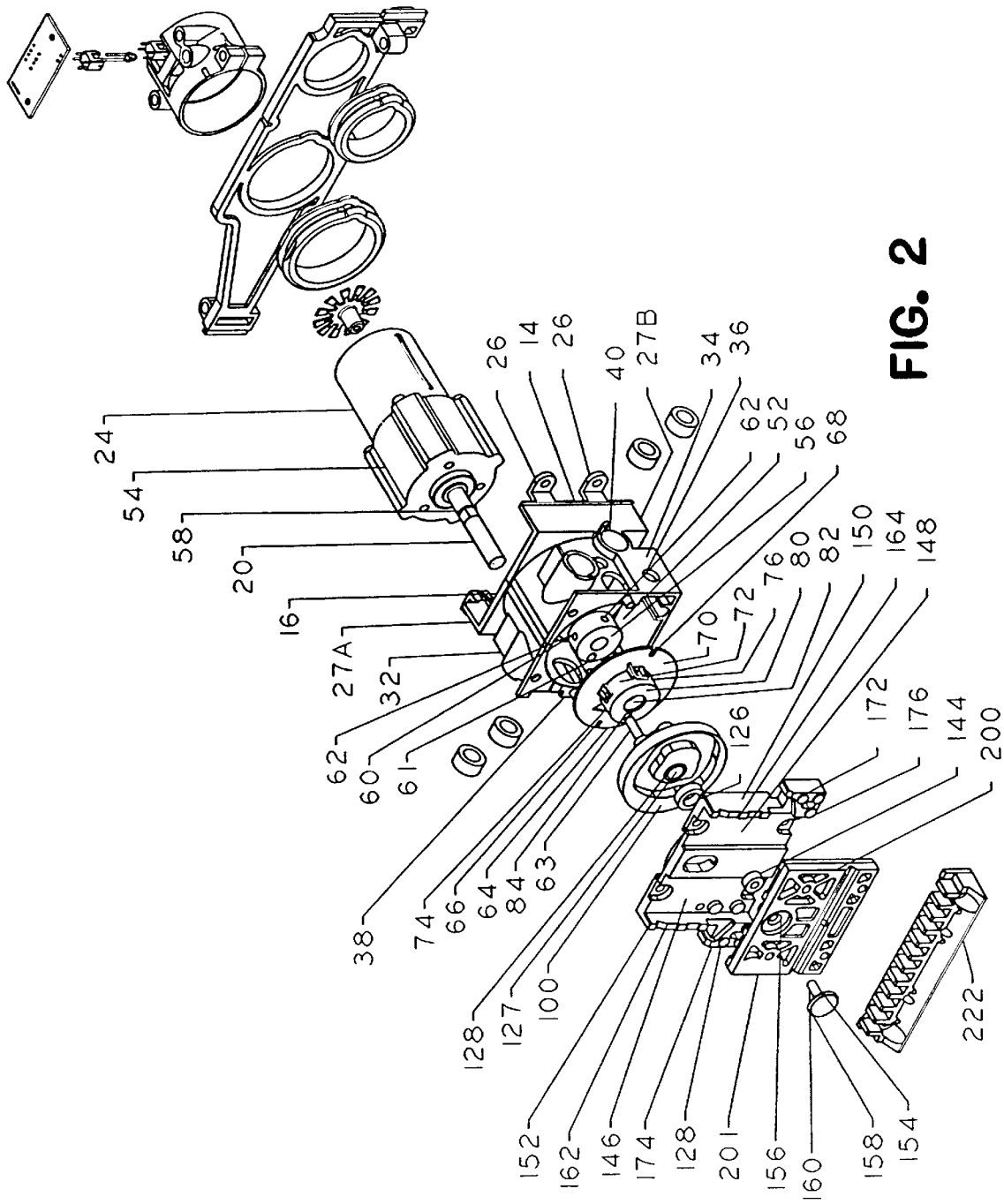
FIG. 2 is an exploded view of the pump sub-assembly.

The pump sub-assembly, as seen in FIG. 2, comprises a housing 14 to which various associated elements are affixed. Housing or chassis 14 is preferably made of a molded plastic so as to speed assembly and fabrication thereof. Chassis 14 further comprises an aft plate 16 formed integral with chassis 14, wherein aft plate 16 has defined therein a plurality of apertures.

Motor shaft aperture 18 is substantially centrally located in aft plate 16 and is operative to allow pump motor shaft 20 to pass therethrough. Aft plate 16 further has defined therein pump motor mounting holes 22 which are spaced radially outwardly from pump motor shaft aperture 18. These holes serve to locate accurately pump motor 24 in combination with the motor bearing boss with respect to the chassis 14. Abaft of the aft chassis plate 16 are a plurality of mounting wings 26 which are operative to securely fix the chassis to the downstream platen 500 located on the downstream side of the chassis 14 and the upstream platen located on the upstream side of the chassis 14; wherein upstream denotes the side of the assembly 10 which is located closer to the fluid inlet thereto and downstream denotes that side of the assembly 10 which is located closer to the fluid outlet therefrom.

Figure 3:
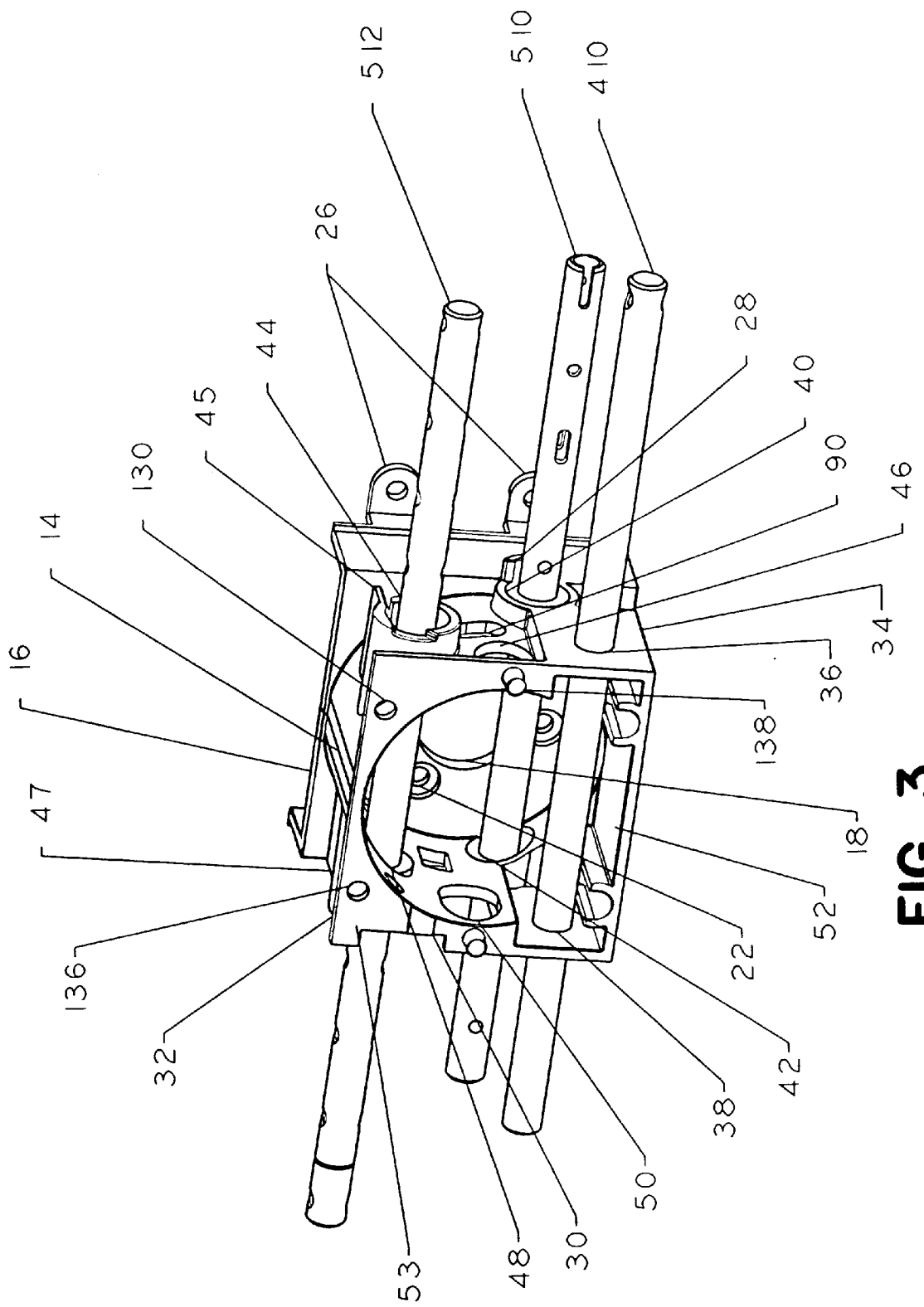
FIG. 3 is an isometric view of the chassis or datum body with the associated datum shafts.

As seen in FIGS. 2 and 3, chassis 14 further defines a plurality of apertures substantially transverse to the pump motor axis 32 which is defined as being coaxial with pump motor shaft 20.

Set before wings 26 is an upstream fluid barrier tab 27A and a downstream fluid barrier tab 27B which are cooperative with the slide clamp actuator support and downstream platen aft plate 580 to provide a fluid shield between the fluid source (IV tube or set) and the associated electrical apparatus located abaft of the combined fluid stop assembly composed of the three elements aforementioned.

These transverse ports or apertures serve to allow access to various mechanisms interior to the chassis as shall be subsequently described and also provide a single datum point to fix the relative locations of the various sub-assemblies which depend from the various parts associated with these apertures. This style of manufacture provides an accurate and robust means of fabricating the pump assembly 10 whilst providing an economy of measured points requiring adjustment to ensure correct operation of the device. These apertures are reproduced on both the upstream sidewall 32 and downstream sidewall 34 of the chassis 14.

The first such aperture set is the valve pivot shaft ports 36, 38 which serve to support and locate the valve pivot shaft 410 relative to the chassis 14.

The second such aperture set supports the tubeloader camshaft 510 and is denoted as the tubeloader camshaft ports 40, 42.

The third such aperture serves to support and locate, relative to the chassis 14, the tubeloader layshaft 512 and is denoted the tubeloader layshaft apertures 44, 48.

The fourth such aperture set serves to allow access of the pump valve cam actuators 422, to the interior of the chassis 14, and is denoted valve actuator ports 46, 50.

The chassis defines a cavity 52 therein which serves to house the pump drive sub-assembly as shown in FIG. 2.

The pump motor 24 is the aftmost element of this sub-assembly. This motor is preferably a variable speed d.c. motor having an internal speed reduction gearbox 54 which in the preferred embodiment provides a 64 to 1 reduction of motor speed.

The output of the pump motor gearbox 54 is pump shaft 20. Pump shaft 20, as aforedescribed, extends axially into cavity 52 via pump shaft aperture 18.

Interior to cavity 52 and in circumferential engagement with pump shaft 20 is drive collet 56. Drive collet 56 has a further mechanical engagement with pump shaft 20 via a combination of a plurality of collet flats 58 which are impressed on shaft 20 so as to provide a polygonal surface operative to engage grubscrews 60 which thread through corlet 56 via threaded grubscrew holes 62 which are situated radially and transversely to shaft axis 32 though drive collet 56. Drive collet 56 further has defined therein a drive pin aperture 61 which is longitudinally parallel and radially outwardly from pump shaft axis 32 and is operative to support and drive fixing pin 63 in concert with movement of collet 56 and motor shaft 20.

Figure 4:
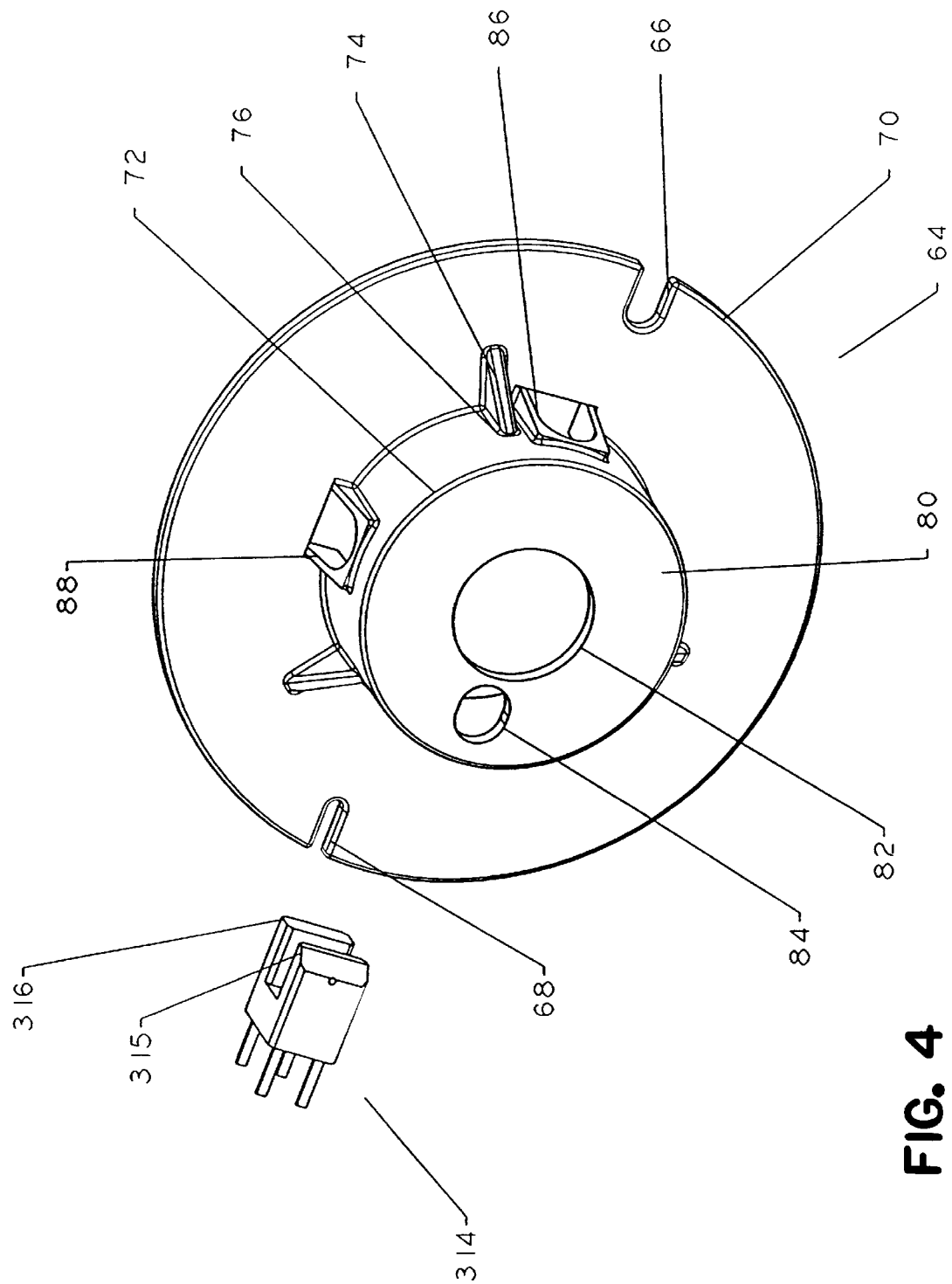
FIG. 4 is an isometric view of the index wheel and the associated sensor.

Surmounting drive collet 56 and coaxial therewith, is the pump index wheel 64, as shown in FIG. 4.

Index wheel 64 is operative, with associated sensors, to determine the location of the pump elements. The index wheel has defined therein a first radial slot 66 and a second radial slot 68, which are about the periphery of index wheel 64. These two slots are located 180 degrees away from each other.

The index wheel 64 is comprised of a wheel disc portion 70 and a hub portion 72 wherein the hub portion 72 is radially interior to and substantially forward of the wheel disc portion 70. The hub portion 72 of the index wheel 64 is connected to the wheel disc 70 by a plurality of webs 74 extensive from the hub 72 to the disc 70. The hub portion further comprehends a cylindrical longitudinally extensive portion 76 and a transverse annular portion 80, wherein the cylindrical portion 76 extends forward of disc plate 70 and the annular portion 80 extends radially inwardly from the cylindrical portion 76 to the motor shaft 20.

Annular portion 80 further defines a motor shaft port 82 which is coextensive with the motor shaft 20 and a fixing pin port 84 located outward from the motor shaft port 82 and parallel therewith. The motor shaft port 82 allows the motor shaft 20 to pass through the index wheel 64 while the fixing pin port 84 enforces co-rotation of the motor shaft 20 and the index wheel 64 when fixing pin 63 is inserted therethrough.

Hub portion 72 has defined therein two access ports 86, 88 which allow access to the collet grub screws 60. These hub access ports 86, 88 are accessible from the exterior of the chassis 14 via set screw access port 90.

Figure 5:
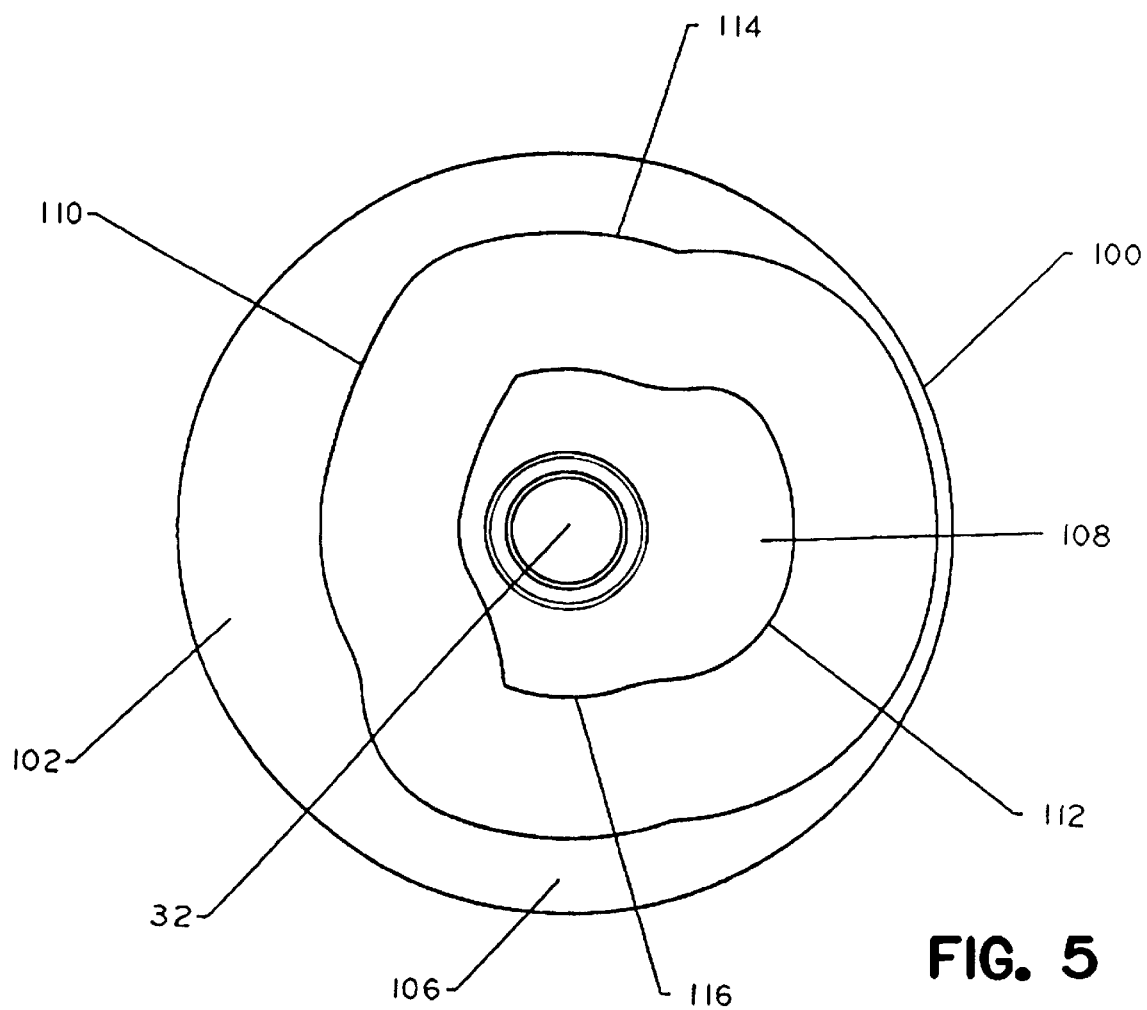
FIG. 5 is a face-on plan view of the pump drive cam.
Figure 6:
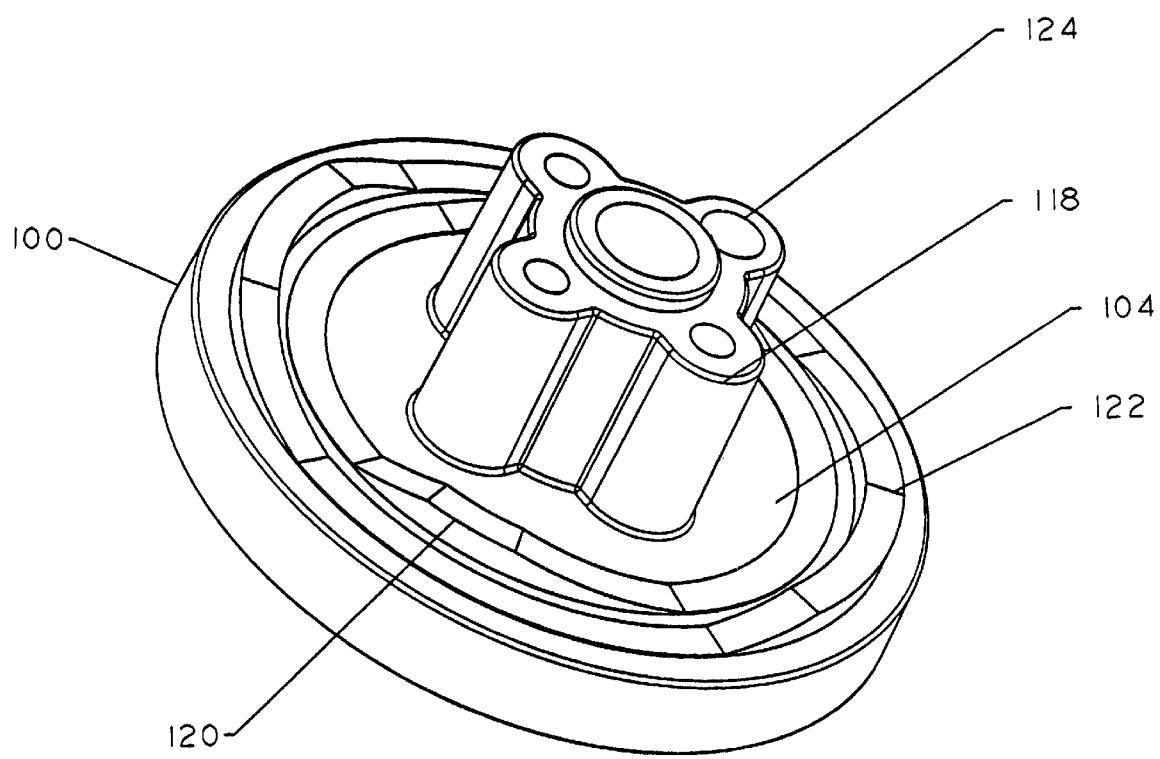
FIG. 6 is an isometric view of the valve cam lands on the main drive cam.

Surmounting the index wheel 64 and forward of the annular portion 80 thereof, resides the pump drive cam 100 shown in FIGS. 5 and 6. Pump cam 100 consists of a front face area 102 and a rear face area 104.

The front face area 102 further comprises an exterior cam land 106 and an interior cam land 108. The exterior and interior cam lands 106, 108 are cooperatively formed so as to provide positive actuation of pump cam follower 110. The shape and aspect of the two lands 106, 108 are non-linear with respect to the variation of distance of various parts of the lands 106, 108 from the pump shaft axis 32.

Figure 7:
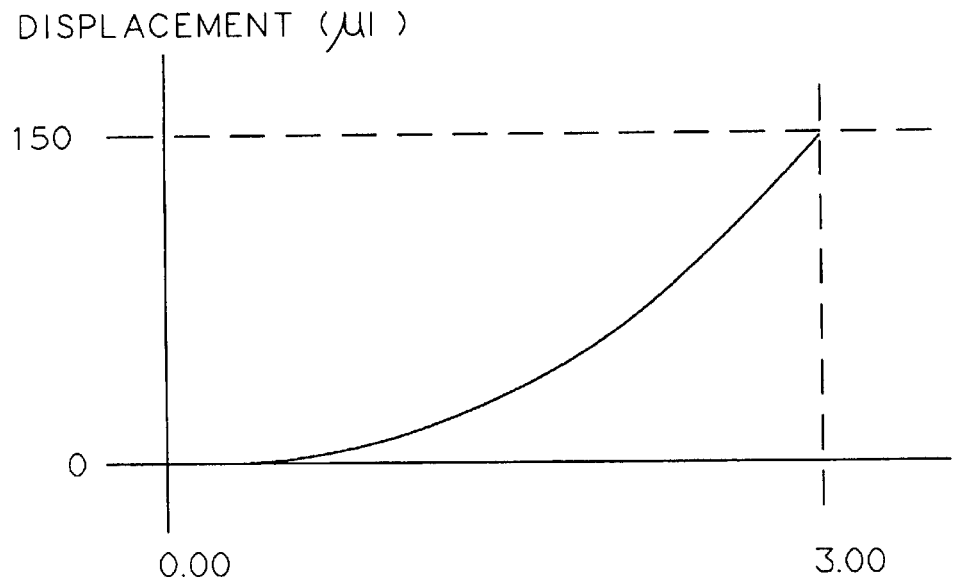
FIG. 7 is a graph showing the relation between linear displacement of the shuttle and volumetric displacement of the tube when there is no linearization of the fluid output.
Figure 8:
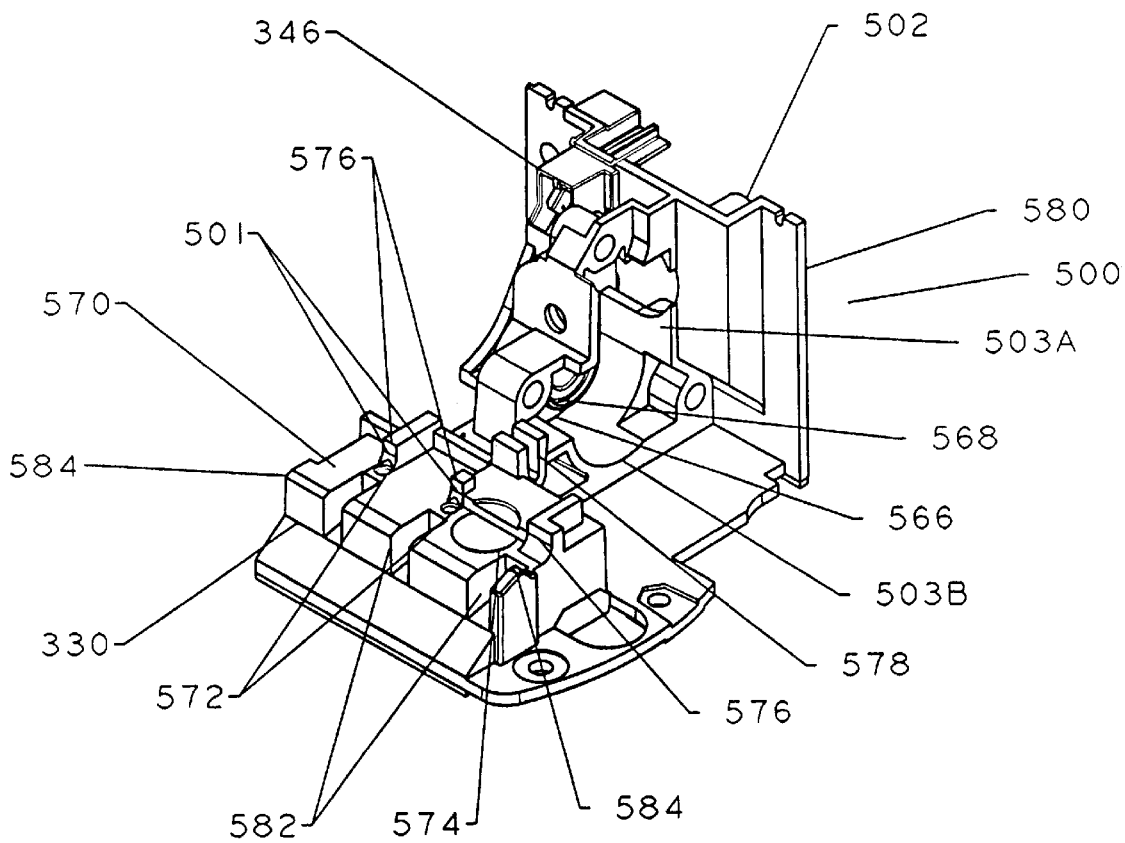
FIG. 8 is an isometric view of the downstream platen.

The rotary to linear motion conversion, as realized by cam 100, introduces non-linear error, as shown in FIG. 7, in the volumetric output of the pump with respect to time (as measured in shaft encoder counts). The aspect of the interior land 108 and the exterior land 106 act cooperatively to achieve a first order correction of this error so as to linearize the output of the pump with respect to volume. This is achieved by an alteration of the change in radial displacement of the cam lands 106, 108 with respect to the motor shaft axis 32 as aforedescribed so as to minimize the effects of angular error on the accuracy of the pump.

Specifically, to a first approximation the cam executes an inverse sine function as determined by the radial distance of the lands 106, 108 from the shaft axis 32.

As can be seen in FIG. 7, the characteristic volumetric output of a tube between two v-grooves executing a relative motion is a non-linear function of displacement of the grooves. This shuttle 200 structure is recited in the Patent to Danby et al, U.S. Pat. No. 5,150,019 corresponding to U.K. Pat. No. 2,225,065 as aforerecited.

As seen in FIG. 5, the alteration of the cam profile, as herein described, provides a markedly more linear output by increasing the shuttle speed during the middle of the stroke (between 30 degrees and 60 degrees of cam angle) and decreasing the speed of the shuttle 200 at the beginning and end of the stroke.

Figure 9:
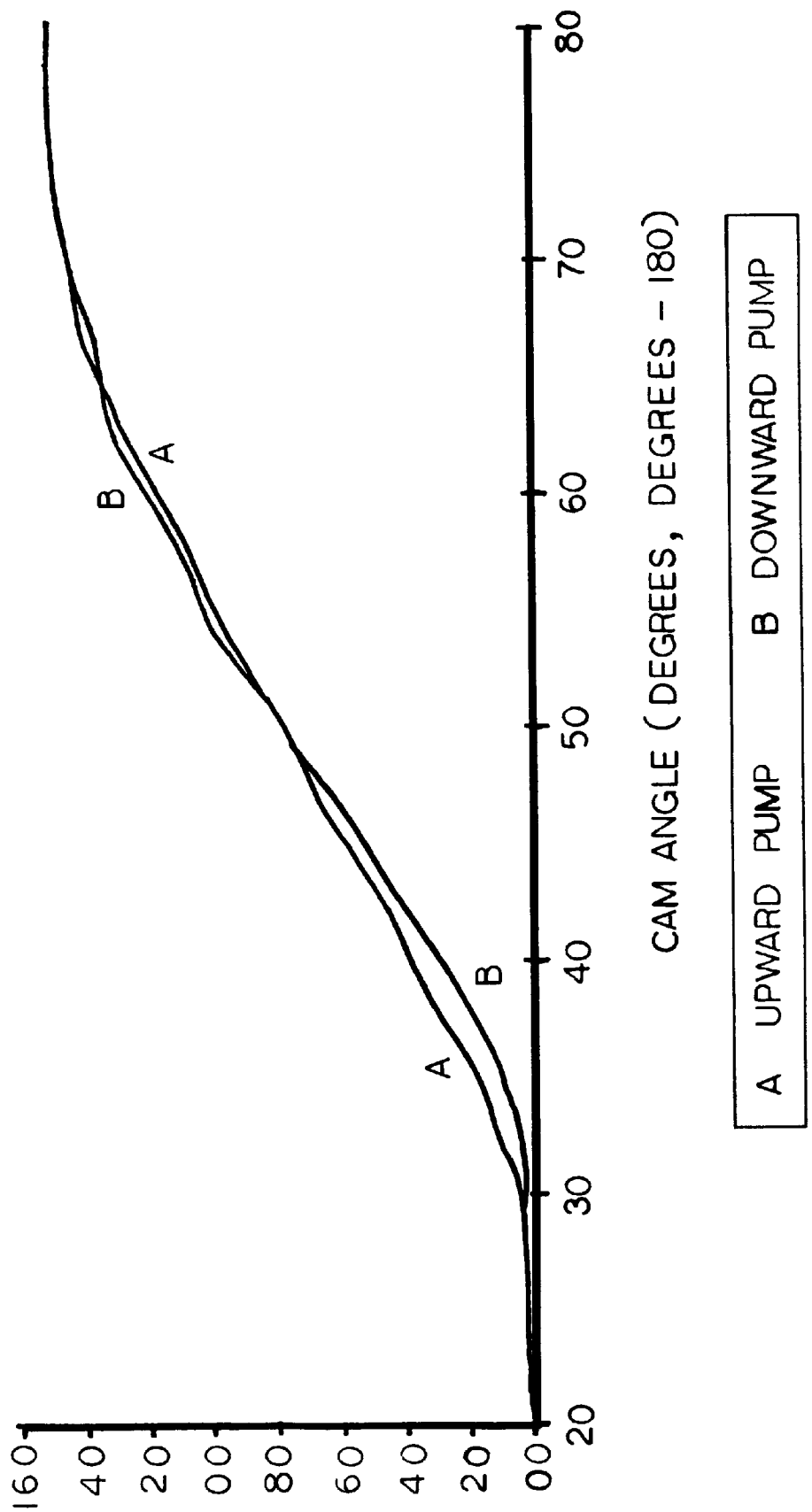
FIG. 9 is a graph of displaced volume of the tube versus cam angle when the cam provides a linearizing correction to the pump displacement.

As seen in FIG. 9, this variable linear velocity provides a significantly more linearised volumetric output wherein output is essentially linear between 30 degrees and 70 degrees of cam angle. The variation between upward and downward strokes being due to use of simple radii within the cam.

Referring now to FIG. 5, which depicts cam lands 106, 108 in face on aspect, shows the various cam positions clearly. As shown, there are two primary pumping portions 110, 112 corresponding to downward and upward movements of the shuttle 200. Also seen are dwell portions 114, 116 which allow the inlet and outlet valves to be actuated as shall be subsequently described.

Further linearization of output is controlled electronically via a position sensitive speed control which shall be subsequently described.

Referring now to FIG. 6, the reverse side 118 of cam 100 is shown. As can be seen, there are two concentric valve cam lands 120, 122. In this embodiment, the inner valve cam land 120 drives the upstream (inlet) valve and the outer valve cam land 122 drives the downstream (outlet) valve. As can be seen, at no time are the inlet and outlet valves simultaneously operated, thereby positively preventing a free flow condition of medicament. The duration and dwell of the valve cam lands 120, 122 are arranged to provide for proper valve synchronization although the inner valve cam race 120 and the outer valve cam race 122 are at differing radii as measured from the pump shaft axis 32.

The rear hub 118 of the drive cam 100 also defines a cam fixing in port 124 which serves to lock the relative location of the drive cam 100 to that of the drive collet 56, via fixing pin 63 and, therefore, to that of motor shaft 20.

Motor shaft 20 is capped by nosebearing 126 which is located immediately afore cam 100. The motor shaft 20 passes through cam 100 via cam motor shaft port 127 defined centrally in the cam 100. Surrounding cam motor shaft port 127 is the forward cam annulus 128 which serves as a lash adjustment for cam 100 float along motor shaft 20 between collet 56 and nosebearing 126.

In the preferred embodiment of the instant invention, nosebearing 126 is a roller type bearing. Nosebearing 126 fits into the nosebearing race 132 in the rear side of the shuttle platen 130.

Shuttle platen 130 is affixed to the forward chassis surface 53 by a plurality of fasteners which connect shuttle platen 130 to forward chassis surface 53 via a plurality of fastener ports 134 defined in the shuttle platen 130 and a second plurality of fastener ports 136 defined in the forward surface 53 of chassis 14. The relative location of the shuttle platen 130 with respect to the chassis 14 is defined by register pins 138 in the forward chassis surface 53 for which corresponding shuttle platen register ports 140 are defined in the back surface of shuttle platen 130.

Shuttle platen 130 additionally has defined therethrough a shuttle drive cam follower throughport 142 which is defined to allow the shuttle actuating cam follower 144 access to the shuttle drive cam 100. The front surface of the shuttle platen 146 defines a plurality of channels 148 in which the shuttle 200 resides. These shuttle platen channels 148 are of a low friction finish so as to allow free movement of the shuttle 200 thereacross. The front shuttle platen surface 146 further defines side rails 150, 152 which are operative to limit torsional movement of the shuttle 200 as the shuttle 200 performs its motion.

Throughport 142, as aforementioned, allows passage therethrough of cam follower 144. Cam follower 144 is an annular roller bearing of such dimension as to allow motion thereof between the pump drive cam lands 106, 108. The shuttle drive cam follower 144 rides on the shuttle drive pin 154 which resides in the shuttle drive pin recess 156 so as to be flush with the front surface 201 of the shuttle 200. The drive pin 154 further comprises a head 158 which is operative to spread drive forces evenly to the shuttle 200 and furthermore, provides an adequate peripheral area for effective press-fit connection thereof to the shuttle 200.

The shaft portion 160 of the shuttle drive pin 154 extends through the shuttle 200 via drive pin port 202 defined therein, and is sufficiently extensive to pass through the shuttle platen 130 and engage shuttle drive cam follower 144.

The shuttle platen 130 completes the datum or register point set based on measuring locations throughout the pump 10 from the chassis 14 and associated components.

Figure 10:
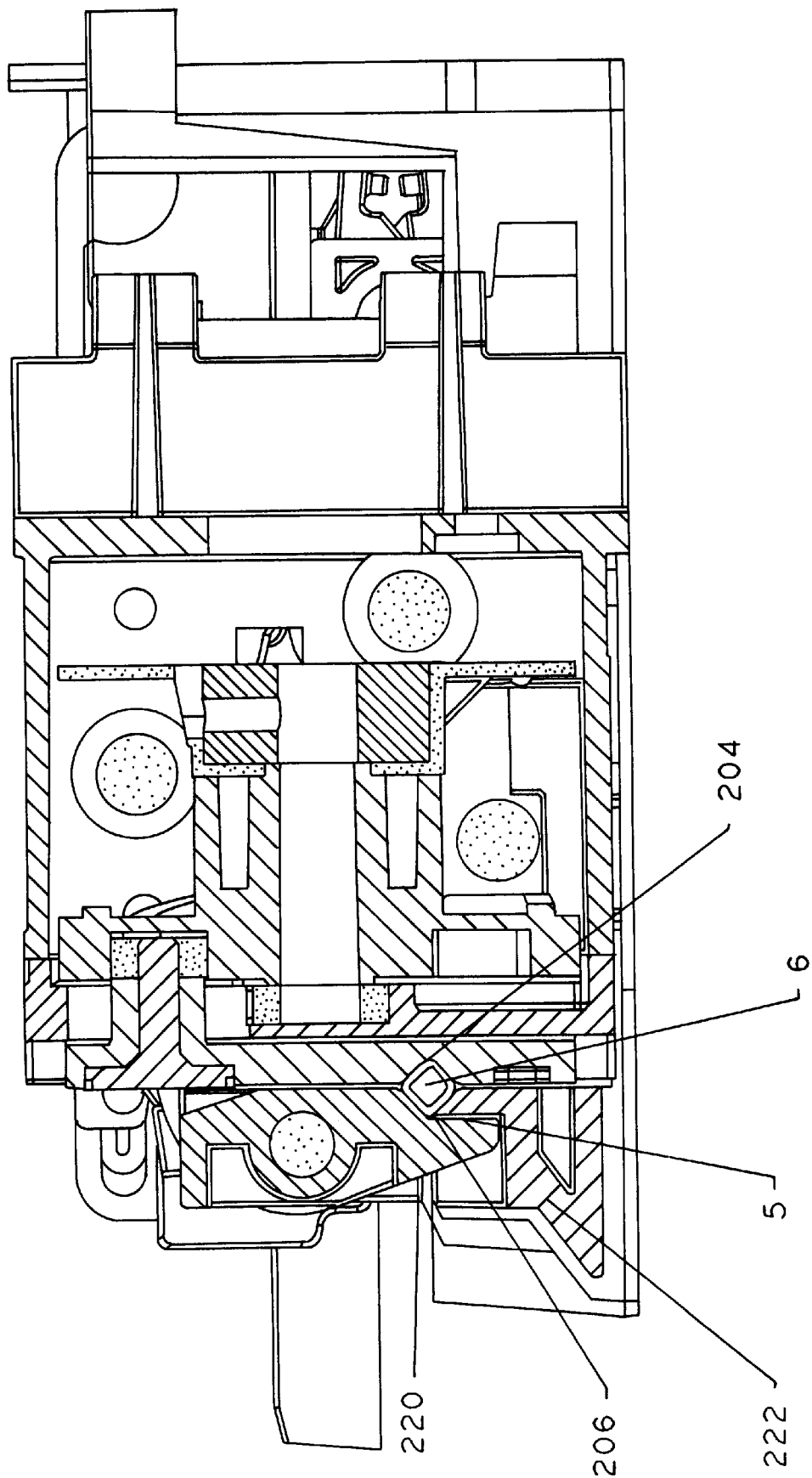
FIG. 10 is a cross-sectional view substantially along line A—A of FIG. 1.

The shuttle platen side rails 150, 152 have forward surfaces 162, 164 upon which are located a plurality of datum surfaces 168, 170. These datum pads 168, 170 are operative to fix the distance from shuttle 200 to that of the upper jaw 220 of the pump assembly. This distance, experiment has found, must be maintained at 0.2 mm. This distance is critical due to the pump geometry wherein, as shown in FIG. 10, the initial deformation of the tube section acted upon by the pump is dependent upon the lateral distance between the moving shuttle indent 204 and the fixed, or non-moving, indent 206 so as to provide a deformation of the initially circular tube cross-section to an equiangular quadrilateral cross-section. This initial deformation bears on the amount of closure of the pump tube lumen 6 as the pump cycles through its stroke; as the stroke throw is fixed by the lift of the drive cam lands 106, 108. The amount of deformation of the pump tube lumen fixes the volumetric output of the pump, per stroke or cycle thereof.

The lower portion of the side rails 150, 152 are laterally extensive beyond the shuttle 200. The forward surfaces of the lower lateral extension 172, 174 have associated therewith a second set of datum pads 176, 178 which are operative to fix the distance of the lower fixed jaw 222 from the shuttle 200. The function of these lower jaw datum pads 176, 178 are similar to the function of the upper datum pads 168, 170 as aforedescribed.

Figure 11:
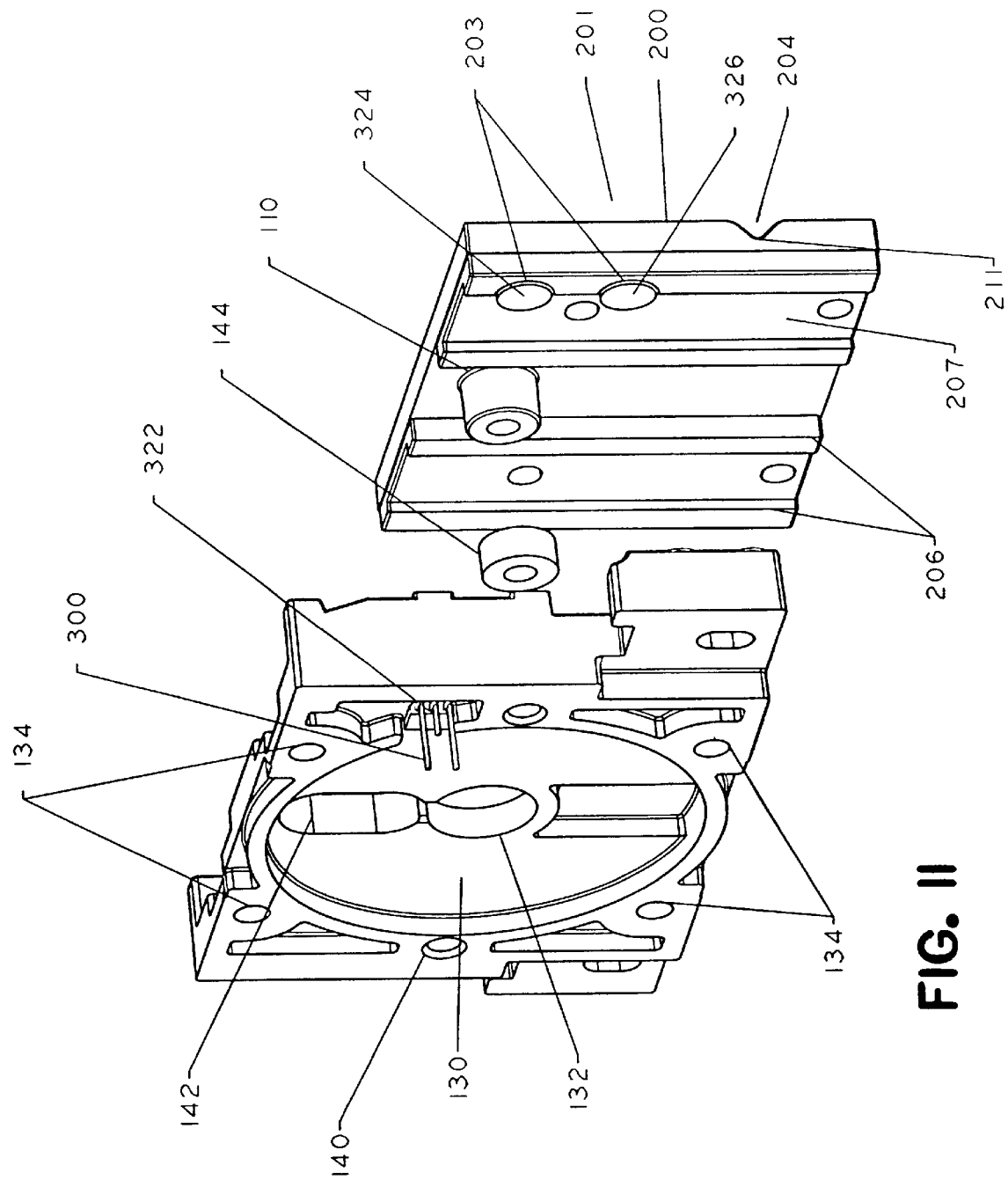
FIG. 11 is an isometric view of the rear of the shuttle platen and shuttle.

Shuttle 200 further comprises, as shown in FIG. 11, a rear side 207 of the shuttle 200. The rear shuttle side 207 further has defined therein a plurality of slide rails 206. The slide rails 206 are operative to provide for a minimization of friction betwixt the shuttle 200 and the shuttle platen 130. The slide rails 206 are in substantially full face engagement with the channels 146A of the shuttle platen 130, and provide a fixation of both longitudinal and lateral lash between the shuttle 200 and the shuttle platen 130.

The front surfaces 201 of the shuttle 200 defines a pump groove aperture 204. This aperture, or indent 204, is of a substantially v-shaped cross-section and has a rounded interior corner 211 so as to provide for a conformation of the tube 5 and the groove aperture 204 when the tube 5 is loaded therein.

The rear surface 207 of the shuttle 200 further has defined therein a plurality of pockets 203 arranged in a substantially vertical array. These pockets 203 are adapted to contain a plurality of magnets which are cooperative with a magnetic sensor 322 to sense the linear position of the shuttle 200.

Sensors Associated with the Pump Sub-assembly

The pump sub-assembly, as previously described, has associated therewith a plurality of sensors which are operative to provide information as to the function and location of the various elements thereof.

The aftmost of the sensors is the drive motor shaft encoder 300. Showing FIG. 12 this sensor comprises an encoder flag wheel 302 which is attached to the armature shaft 303 of motor 24. The pump motor flag wheel 302 has, in the preferred embodiment of the instant invention, twelve flags 304 extending radially outwardly from the hub 306 thereof.

Figure 12:
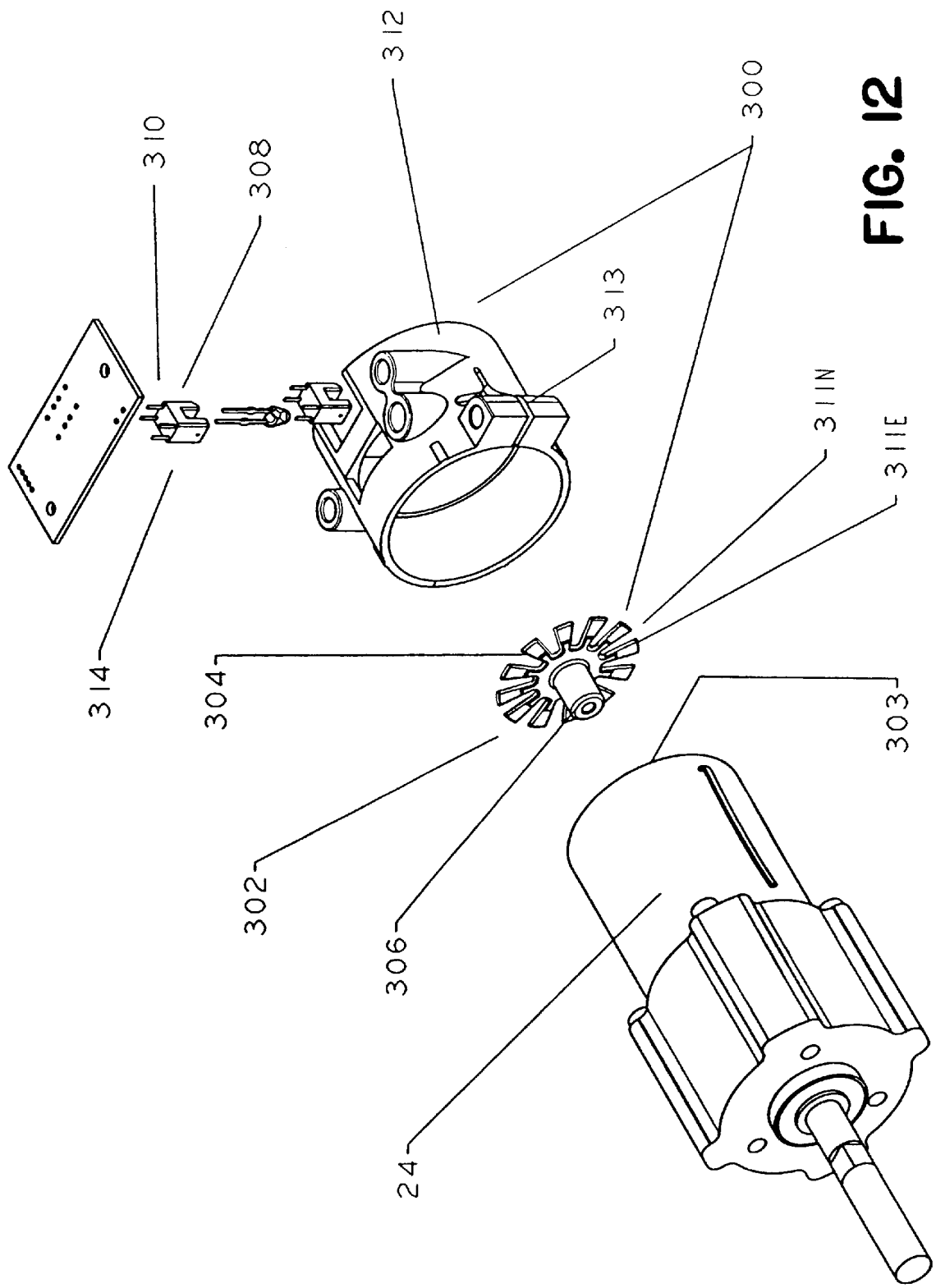
FIG. 12 is an exploded view of the pump motor encoder.

These flags 304 act in concert with two optical switches 308, 310 to fix the location of the armature shaft 303 of the pump drive motor 24. The switches 308, 310 further consist of a light emitting diode and a photocell as shown in FIG. 12. The arrangement of the optical switches 308, 310 allows for a first switch 308 to sense the edge 311E of flag 304, and the second switch 310 to sense the middle 311M of a subsequent flag 304. This arrangement allows for greater resolution of motor shaft position and direction as read by the encoder 300.

In this presently preferred embodiment, the resolution of encoder 300 is $\frac{1}{3072}$ of a rotation of motor shaft 20. The encoder assembly 300 resides in a pump motor encoder support collar 312 which is a sliding fit over motor housing 24 and is affixed thereto by pinch clamp 313.

The motor encoder 300 senses armature shaft 303 rotation directly. However, as there are mechanisms resident between the armature shaft 303 and the shuttle 200, further sensors are desired.

Moving forward along motor shaft axis 32, one returns to index wheel 64. As aforementioned, index wheel 64 has a plurality of circumferentially coextensive radially disposed slots 66, 68. Associated with these slots is an index wheel optical sensor 314. This sensor comprises a light emitting diode 315 and an optical sensor or switch 316.

The index wheel sensor 314 is cooperative with the index wheel 64 and the slots 66, 68 therein to provide positional information of the rotational location of the pump motor shaft 20.

In operation, the index wheel sensor 314 acts in concert with the pump encoder 300 to provide this positional information as well as directional information of the motor shaft 20. The index wheel sensor times the passage of each of the slots 66, 68 past the index wheel switch 314. The two slots 66, 68 are of differing widths so as to provide information as to whether the shuttle 200 is beginning the upstroke thereof or the downstroke thereof, where a first width indexes the upstroke and a second width indexes the downstroke.

Associated with the shuttle 200 itself is a linear gross position sensor 320. This sensor comprises a linear position Hall effect sensor 322 and a plurality of magnets 324, 326. Shuttle position sensor magnets 324, 326 present opposite poles to the shuttle Hall switch 322, so as to provide a field gradient operative to provide an indicium of the linear position of the shuttle 200.

The combination of the encoder 300 and the other associated sensors aforementioned, provide inputs to a control mechanism, which may operate more than one pump so as to accurately control the speed of variable speed motor 24, the primary feature provided by such speed control is a temporal variability of the output of the pump 10. Additionally, such speed control allows for an electronically controlled linearization of the pump output per individual stroke as well as improving the time integrated output of the pump 10. In the preferred embodiment the per stroke linearization of output is realized in combination with the drive cam 100 as aforementioned. The time integrated output of the pump is made more accurate by the pump speed being markedly increased at such points as would provide for a discontinuity in the output profile as measured with respect to time so as to minimize the effects of such discontinuities in output.

As a manufacturing convenience, both the shuttle linear position sensor 320 and the index wheel sensor 314 are electrically connected to the associated signal processing electronics by a shared printed circuit strip denoted as the pump sensor circuit strip.

The Valve Sub-assembly

Figure 13:
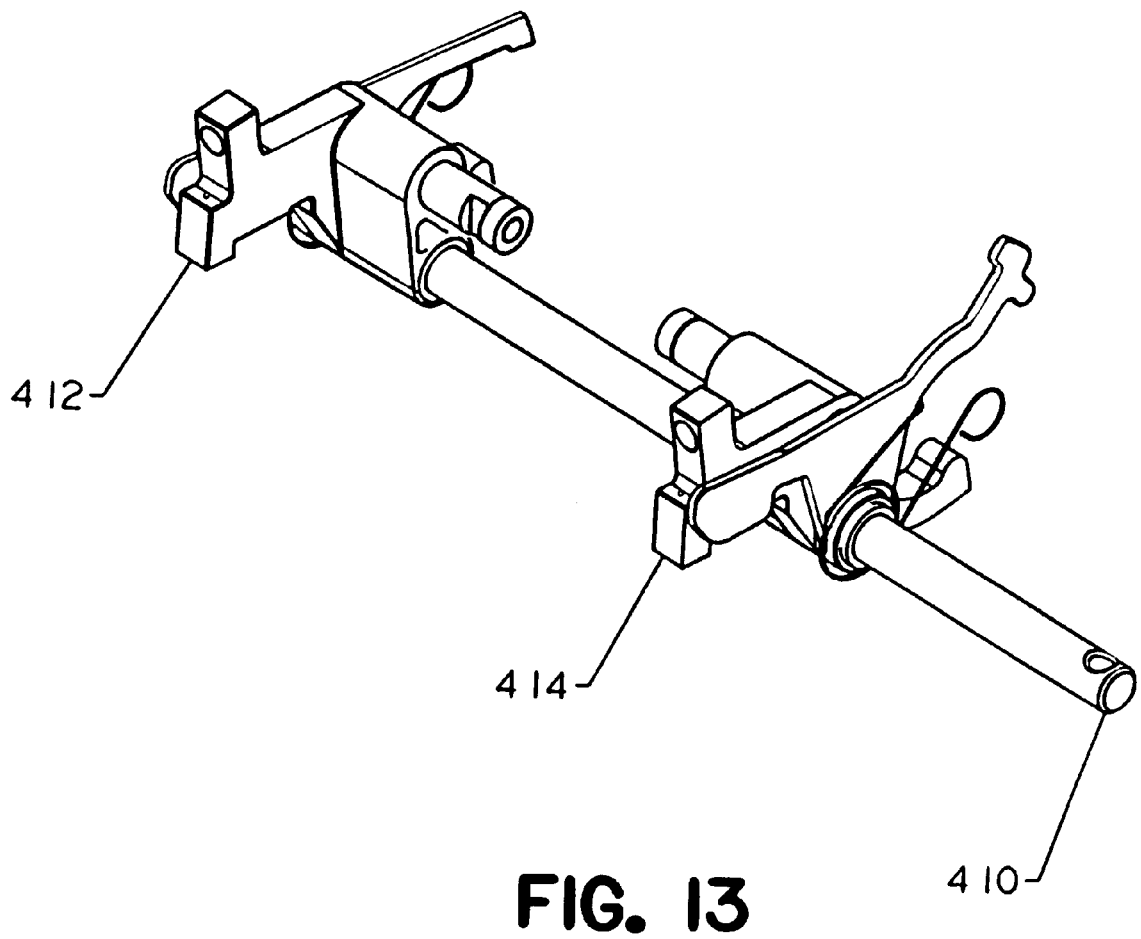
FIG. 13 is an isometric view of the valve sub-assembly.
Figure 14:
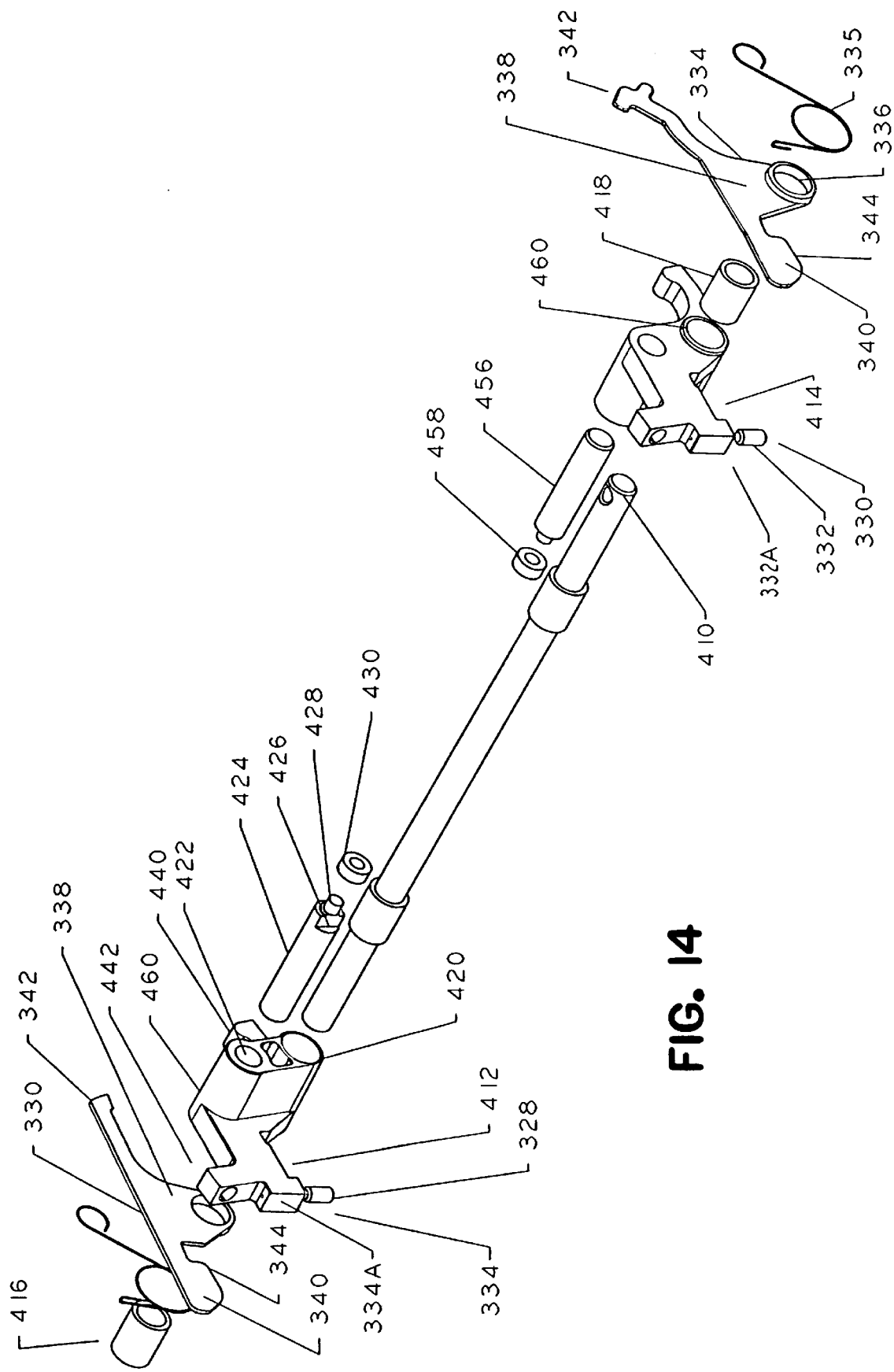
FIG. 14 is an exploded view of the valve sub-assembly as shown in FIG. 13.

The valve sub-assembly is shown, removed from the associated pump sub-assembly, in FIGS. 13 and 14. The valve sub-assembly consists of a valve pivot shaft 410 which is carried by chassis 14 by being supported thereby in pivot shaft ports 36, 38. Valves 412, 414 pivot about this shaft 410 and are supported thereon by valve pivot bearings 416, 418 which are clearance fit onto pivot shaft 410 and into valves 412, 414.

The two valves 412, 414 are denoted individually as the upstream valve 412 and the downstream valve 414. The upstream valve 412 comprises a pivot bearing aperture 420 adapted to accept thereinto the upstream valve pivot bearing 416 and thereby pivot about valve pivot shaft 410. The upstream valve 412 further comprises an upstream valveshaft aperture 422 which is located axially parallel to the pivot shaft 410 and substantially vertically displaced therefrom. The upstream valveshaft aperture 422 is adapted to slidingly receive the upstream valveshaft 424 therein. The upstream valveshaft 424 extends laterally from the upstream valve 412 and is disposed to enter into the chassis 14 via upstream valveshaft aperture 48. The upstream valve actuator shaft 424 is substantially cylindrical and has defined therein an outer cam race cutout 426. The outer cam race cutout 426 is operative to allow the upstream valve actuator 424 to clear the outer or downstream valve race 122 defined on cam 100. The upstream valve actuator 424 terminates in a cam follower nub 428, which is adapted to support the upstream valve roller cam follower 430. The upstream cam follower 430 is, in the preferred embodiment, a roller bearing so as to provide rolling contact between the valve cam land 120 and the upstream valve actuator 424.

Figure 15A:
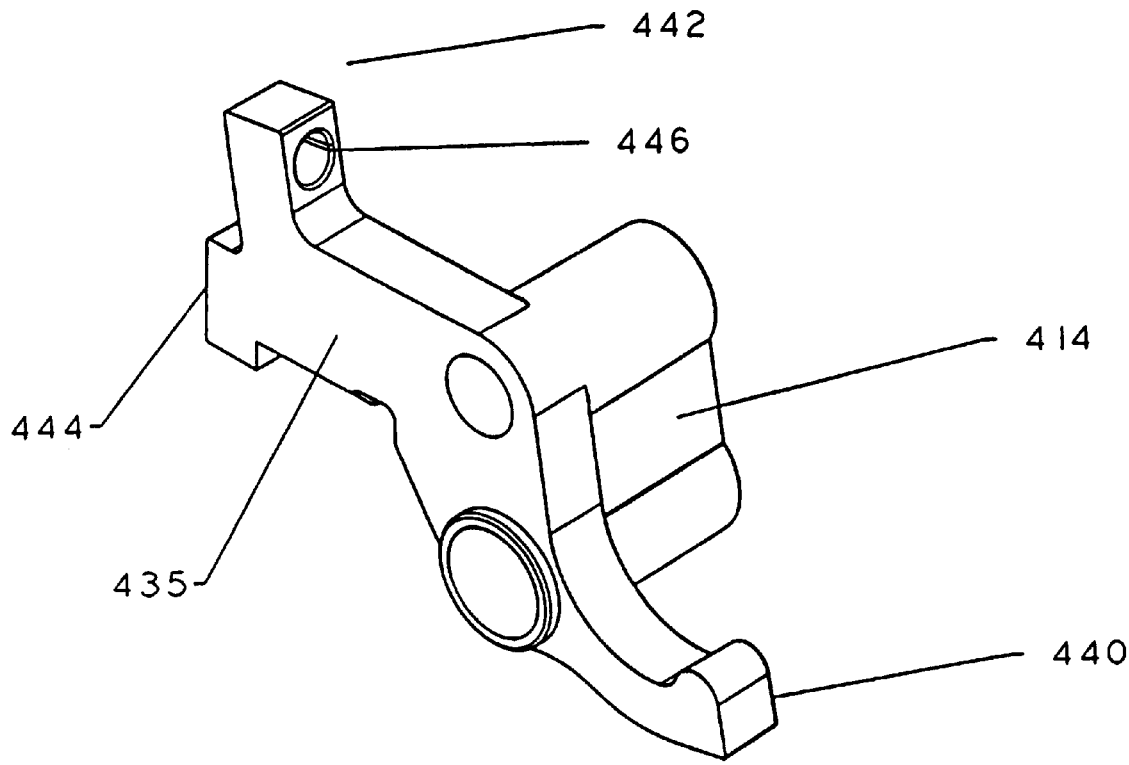
FIG. 15A is an isometric view of substantially the rear and side of one of the valves.
Figure 15B:
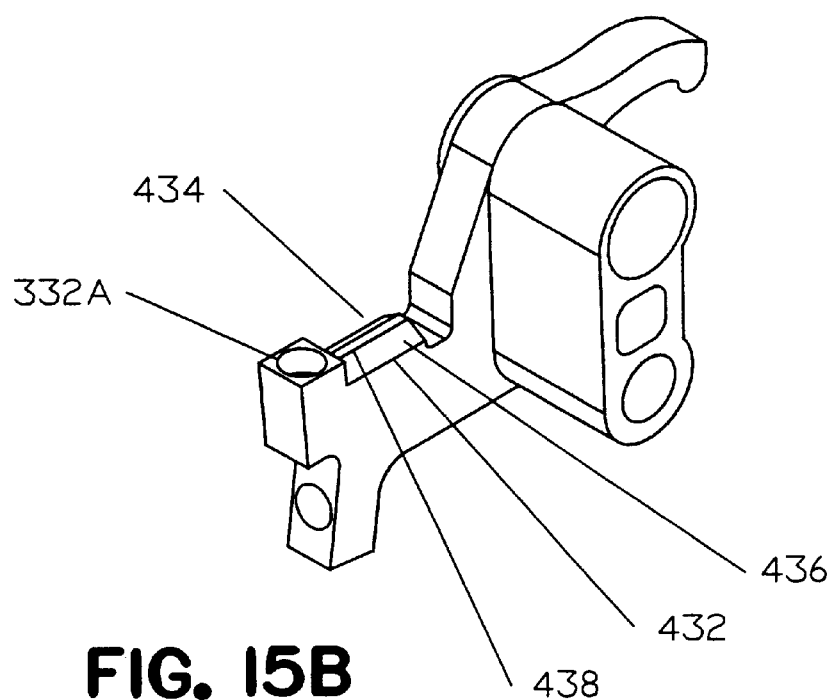
FIG. 15B is an isometric view showing substantially the bottom or tube-facing side of one of the valves.

Returning to valve 412 or 414, the valve further comprises a valve blade 432, as shown in FIG. 15B, which is of a substantially v-shaped cross-section wherein the first side of the valve blade 434 and the second side of the valve blade 436 subtend an angle of approximately 90 degrees therebetween and also define a 0.5 millimeter rounded vertex 438. The combination of the included angle and the rounded vertex 438 provide for an optimal arrangement between the conflicting necessities of ensuring that the tube 5 is sealed during the appropriate part of the pump cycle while simultaneously ensuring that the tube will reform into an accurate approximation of its initial shape when the valve blade 432 is lifted from the tube 5.

The rounded vertex 438 of the valve blade 434 defines a 0.5 mm curvature. This curvature, in combination with the 0.7 mm distance between the valve blade 434 and the valve anvil 570, to be discussed subsequently, provide for an optimization of the two necessities of ensuring sealing while providing for elastic recovery of the tube during the appropriate part of the pump cycle.

Additionally, the tube 5, due to its deformation by the shuttle 200 in combination with the upper and lower jaws 220, 222, comprehends a partial vacuum within that portion of the tube lumen 6 located adjacent to shuttle 200, and the opening of the inlet valve 412 with the positioning of the shuttle 200 providing conditions conducive to assist hydrodynamically the elastic recovery of the tube section below the inlet valve 412.

The upstream valve body 412 further comprises a valve lifting tang 440 which is cooperative with a valve loading cam to raise the valve during the tube loading operation. The valve body 412 comprehends a valve spring seat tang 442 which extends upwardly from the distal end 444 of the valve blade arm 435. The valve spring tang 442 defines a valve spring retainer port 446 which is operative to provide support for the distal end 448 of the valve spring retainer 450. The valve spring retainer 450, in combination with valve spring tang 442, serves to completely capture the valve spring 452 therebetween. The valve spring retainer 450 comprises a substantially c-shaped base 454 which is operative to slidingly fit about the tubeloader layshaft 512, to be described subsequently. The valve spring retainer base 454 is designed to permit oscillatory motion of the retainer 450 about the aforementioned tubeloader layshaft so as to accommodate the motion of the valve 412, 414.

The downstream valve 414 is resident on the valve pivot shaft 410 adjacent to the shuttle 200. The downstream valve 414 is essentially a mirror image of the upstream valve 412 about a plane transverse to the pivot shaft 410 and displays all of the associated elements of the upstream valve 412 in a reversed orientation as seen in FIG. 14. The downstream valve actuator arm 456 is shortened to align the downstream valve cam follower 458 with the outer valve cam land 122.

The action of the two valves 412, 414 is such that at no time during the pump cycle are both valves open at the same time. Furthermore, as both the valves 412, 414 and the shuttle 200 are driven by a single motor 24 and off of a single drive cam body 100, exact synchronization of the valves 412, 414 and the pump shuttle 200 is positively achieved by wholly mechanical means.

Sensors Associated with the Valve Sub-assembly

Associated with each of the valves 412, 414 is a valve motion sensor 328, 330. Each of these valve motion sensors 328, 330 is actuated by a magnet 332, 334 which is inserted into a valve sensor magnet port 332A, 334A in the outboard end 444 of the valve blade tang 435. Located therebelow, in the associated valve anvil and outwardly located therefrom is the valve motion sensor Hall switch 328, 330 which, with associated software, linked to the output of the valve sensor switches 328, 330 to that of the drive motor encoder 300, serves to stop the pump 10 and activate an alarm if a valve 412, 414 is not operating correctly. This is essentially accomplished by comparing the expected output of the appropriate valve sensor 328, 330 with the expected signal therefrom at a specific motor 24 and drive cam location.

Figure 17:
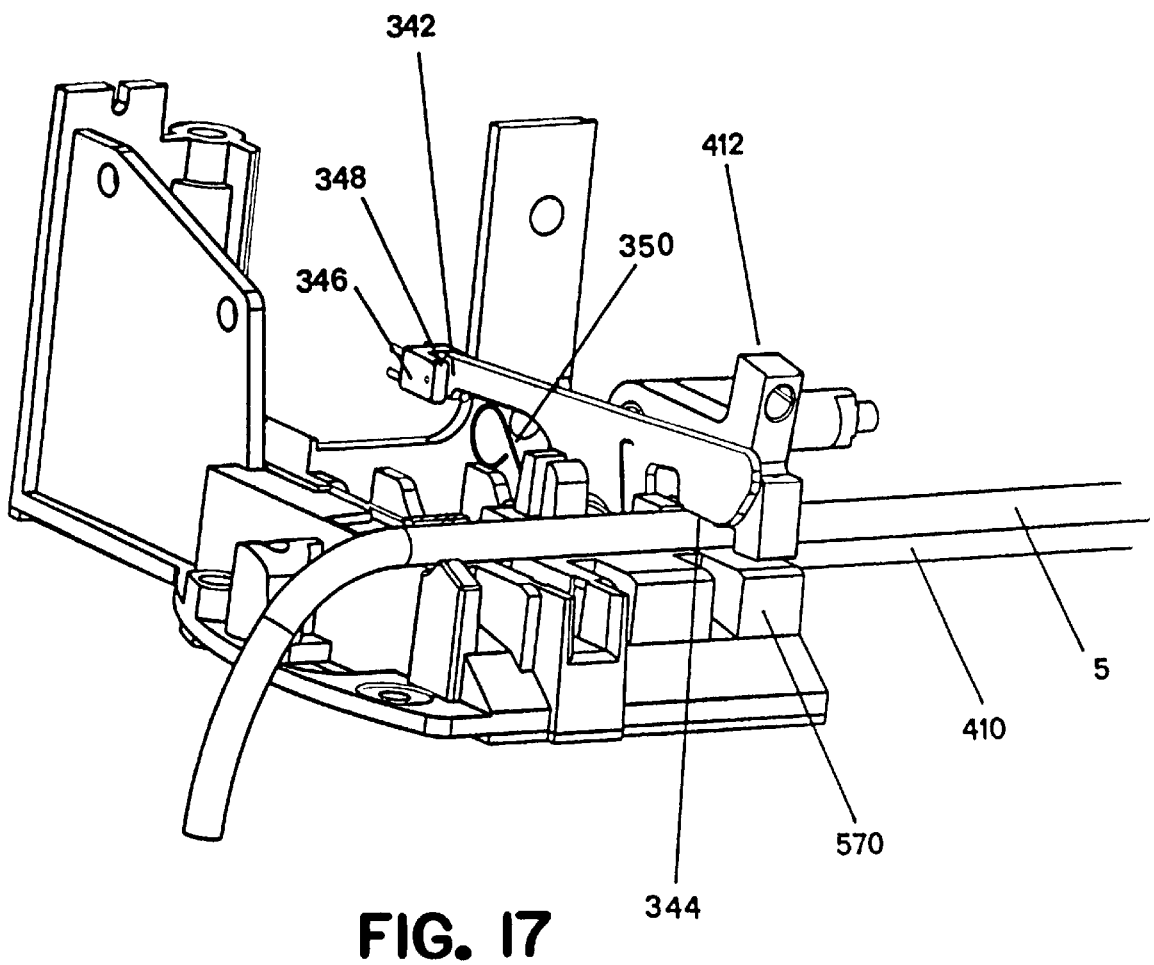
FIG. 17 is an isometric view of the upstream platen showing the tube-present sensor in contact with a tube.

Residing outwardly from each valve 412, 414 and separated therefrom on valve pivot shaft 410 by tube present arm spacers 460 is the tube present sensor arm 340. The upstream tube present sensor, in conjunction with the downstream tube present sensor, serves to determine the actual physical presence or absence of the IV tube in the pump 10. Each of the tube present sensors 332, 334 comprises an annular bearing or tube sensor pivot 336 which surrounds and rides on the valve pivot shaft 410. The tube sensor arm web 338 extends outwardly from the tube sensor pivot 336 and serves to support the tube sensing blade 340 which extends forwardly from the sensor arm web 338 and the tube sensor flag 342 which extends substantially rearwardly from the sensor arm web 338. The sensor blade 340 comprises a downward extension thereof so, when installed, the sensor blade tip 344 resides on the appropriate valve anvil. The insertion of a tube 5 between the blade tip 344 and the valve anvil will, therefore, serve to raise the blade 340 away from the anvil 570 and cause the sensor arm to pivot about the valve pivot shaft 410. This serves to lower the rearwardly extending valve sensor flag 342 thereby interrupting the tube present sensor optical switch 346 by the flag 342 moving into the interstice 348 of the tube present sensor optical switch 346 and interrupting the light beam extending thereacross, as shown in FIG. 17. A return spring 350 serves to bias the tube sensor arm to a position wherein, should the tube 5 not be present, the tube sensor blade tip 344 rests on the associated valve anvil.

The Tubeloader Sub-assembly

Figure 18:
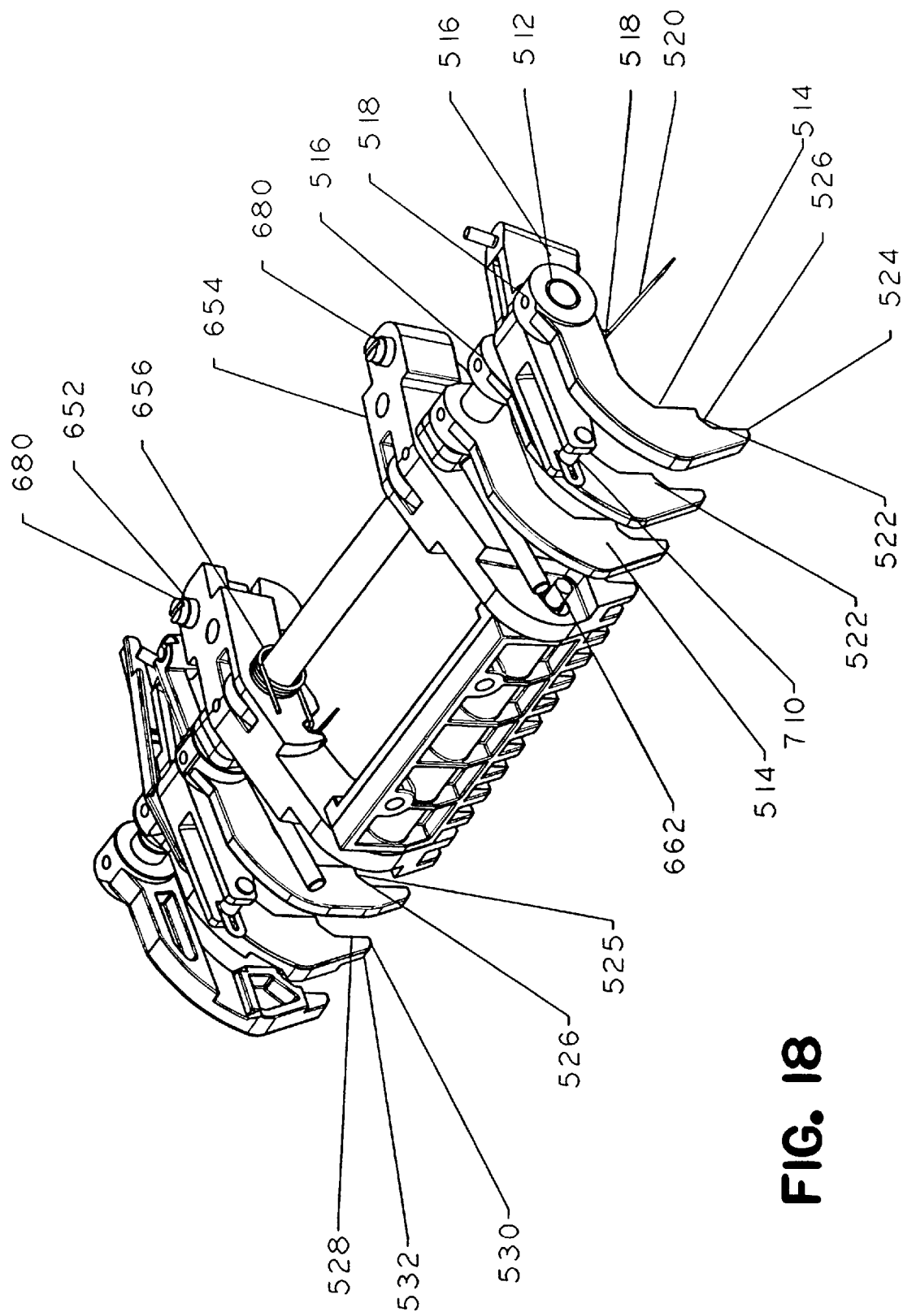
FIG. 18 is an assembled view of the tubeloader sub-assembly.
Figure 18B:
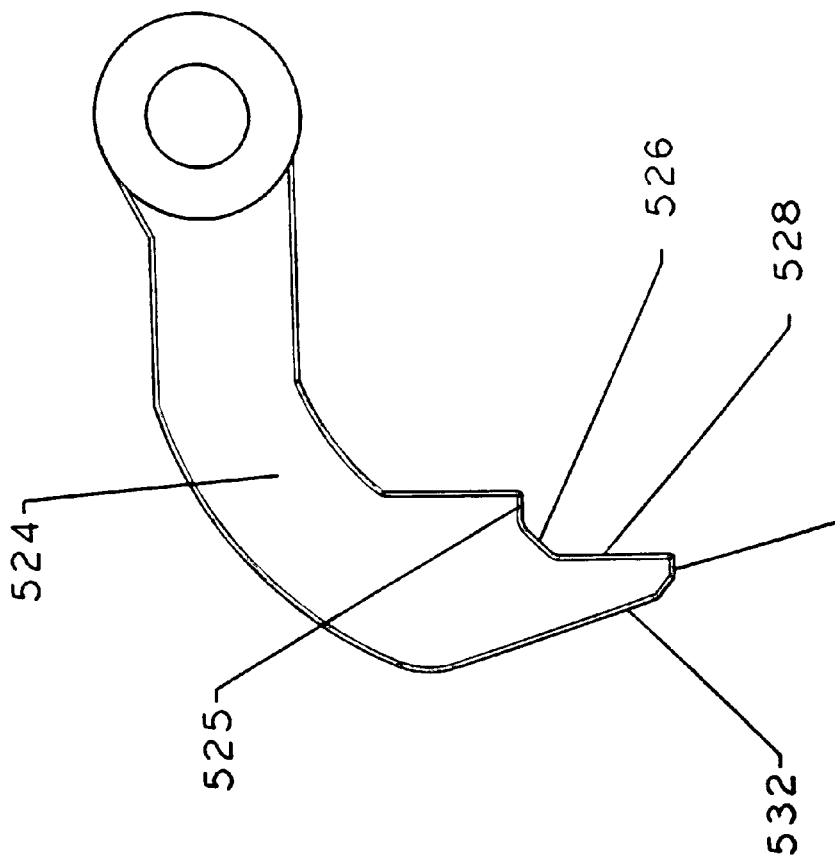
FIG. 18B is a plan view of a tubeloading pawl.
Figure 18A:
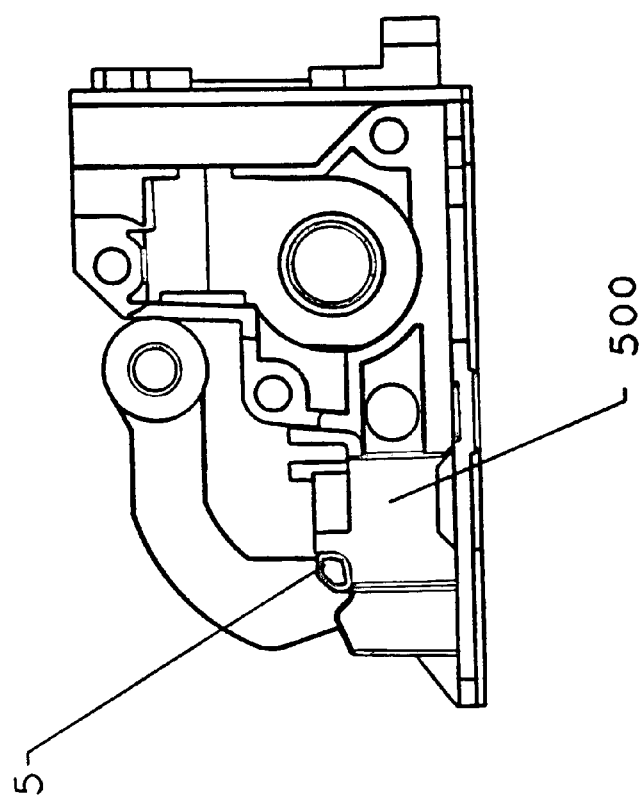
FIG. 18A is a plan view of the downstream platen showing a pawl in engagement with a tube.
Figure 19:
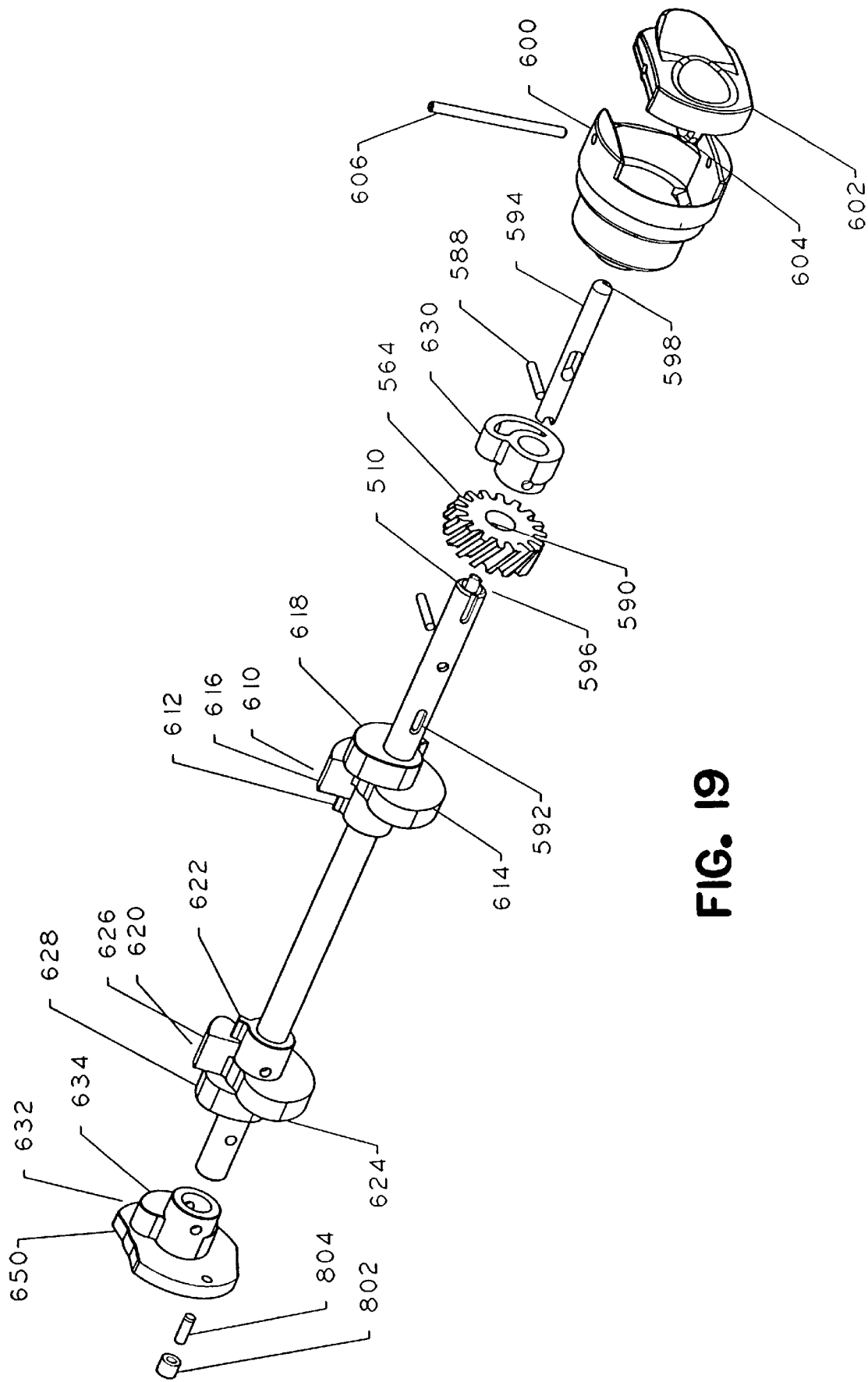
FIG. 19 is an exploded view of the tubeloader camshaft.
Figure 19A:
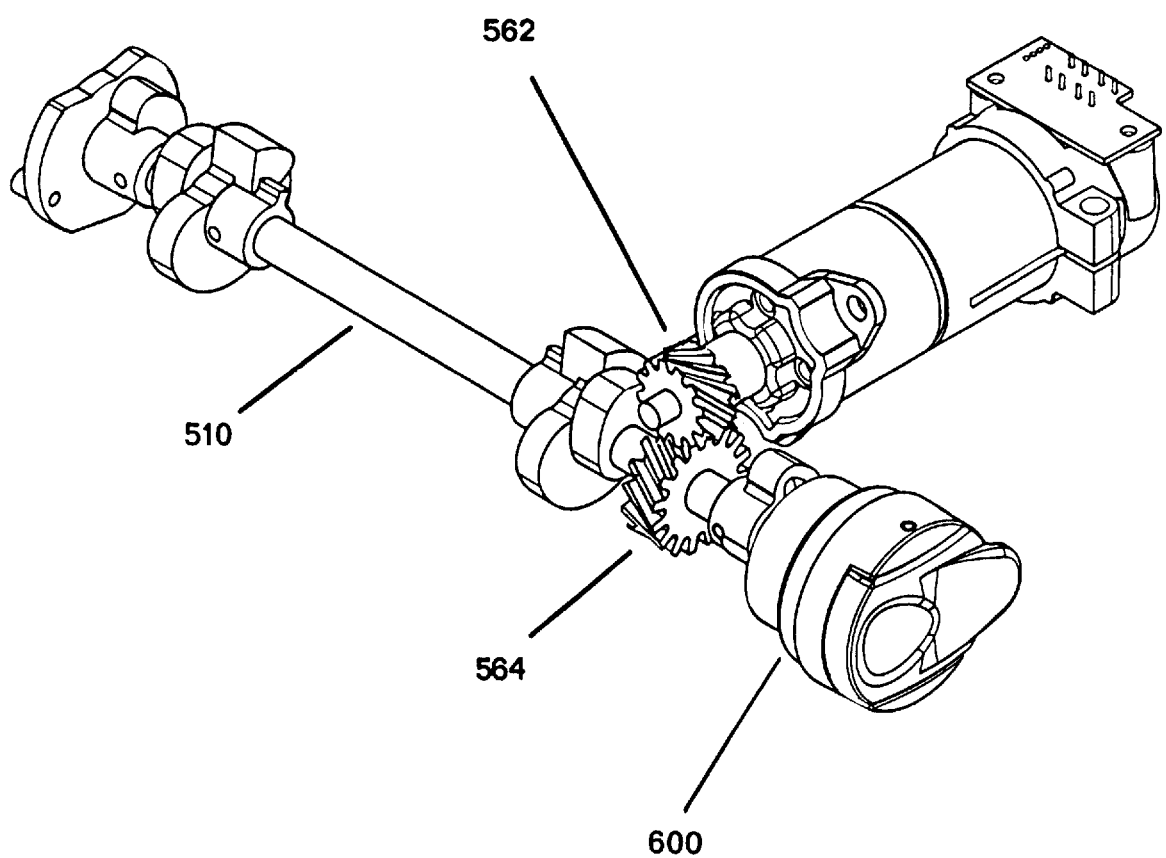
FIG. 19A is an assembled view of the tubeloader camshaft and tubeloader motor.
Figure 20:
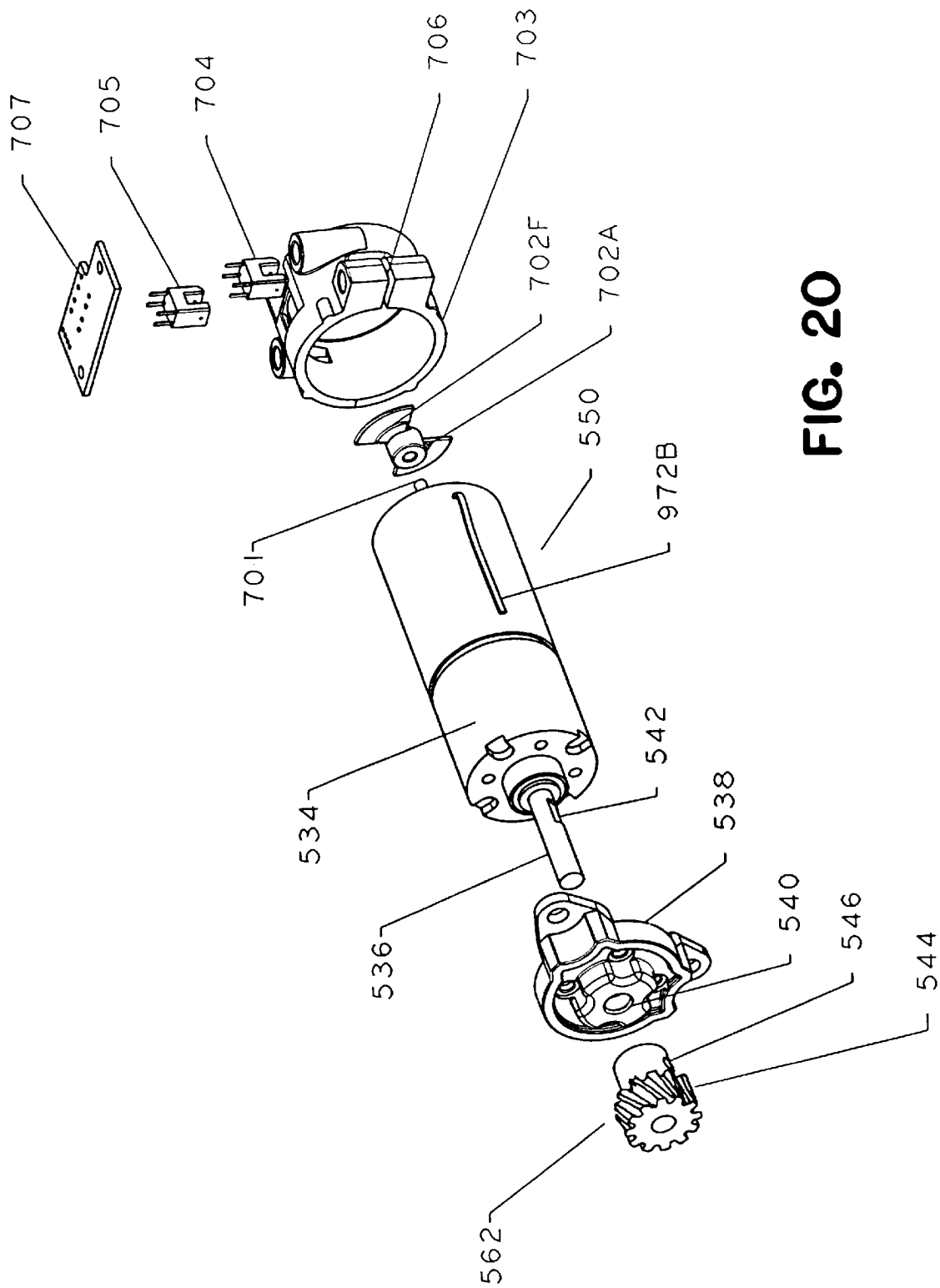
FIG. 20 is an exploded view of the tubeloader motor and encoder.

As shown in FIGS. 18 and 19, the tubeloader sub-assembly utilizes two shafts associated with chassis 14. These two shafts are the tubeloader camshaft 510 and the tubeloader layshaft 512. These two shafts 510, 512, in conjunction with the valve pivot shaft 410, provide the primary datum points for the relative locations of the various assemblies and associated elements thereof, throughout the pump. The locations of these three shafts is shown in FIG. 3. By referencing all points in the pump to these shafts, and thereby to the chassis 14, the pump structure can be indexed without the necessity of a wide variety of precision machined parts, whilst maintaining the requisite accuracy of the completed assembly.

The tubeloader layshaft 512 provides an axis about which all parts which are driven by camshaft 510 rotate save the valves and slide clamp. Moving upstream along layshaft 512, the most outboard of the elements associated therewith are the downstream tubeloader pawls 514. The downstream tubeloader pawls each consist of an annular body 516 which is adapted to ride on the tubeloader layshaft 512 and is fixed thereto by the associated helical pin 518 which extends through the pawl annulus 516 and the layshaft 512 and into the opposed area of the annulus, thereby positively fixing the associated pawl 514 to the layshaft 512. Extending forward of the pawl annulus or collect 516 is the pawl arm 518. The pawl arm has a substantially linear section 520 and an arctuate section 522 extending outwardly and downward from the pawl collet 516.

The shape of the arctuate section 522 of the pawl 514 is such that when the pawl 514 is fully lowered, the tube 5 is firmly wedged against the downstream platen 500, thereby encircling the tube 5 between the pawl 514 and platen 500.

In greater detail, the interior angled surface 526 of the pawl tip 524 intersects the tube 5 at an approximately 45 degree angle with respect to horizontal and is thereby operative to urge the tube 5 downwardly and inwardly against the tube detent 501 in the downstream platen 500.

The pawl tip 524 encompasses a plurality of areas. The interior side of the tip defines a horizontal tube engaging surface 525, an angled tube engaging surface 526, a vertical tube capture surface 528, a horizontal tube misload activating surface 530 and an externally facing tube rejection surface 532 on the exterior side thereof; and the aforementioned surfaces are disposed on the periphery of the pawl tip. These surfaces operate in concert with the downstream platen 500.

The design comprehended by tubeloader pawl tip 524 is repeated on the lower edge of the upper pump jaw 220 and serves an identical function as shall be described herein.

When an operator is loading a tube into pump 10 and actuates the tubeloading cycle by means of an appropriate actuator, or a control button or switch, the tubeloader pawl tips 524 are lowered over tubeway 8 which, in combination with the lowering of the upper jaw 220, serves to completely close off the longitudinal slot or opening on the outboard side of tubeway 8. Should a tube be partially inserted into the pump 10, yet remain wholly outside the tubeway 8, the tube reject surface 532 will operate in combination with nesting slots 582, which are also resident on lower jaw 222, to expel the tube 5 from the pump. In the event of a tube 5 being loaded partially within the tubeway and partially exterior thereto, the misload activating surface 530 will serve to pinch the tube 5 between the misload activating surface 530 and the associated section of either the downstream platen 500, the upstream platen 800, or the lower jaw 220 and thereby actuate a misload detection as described herein. Another possibility contemplated in the design of the pawl tip 524 is wherein the tube 5 is inserted into the tubeway 8 yet has not been fully drawn into contact with the tubestops 576. In this event, the tube capture surface 528 will serve to draw the tube 5 rearwardly and into contact with the tubestops 576 and thereby execute a correct loading of the tube. The combination of the tube reject surface 532, the misload activating surface 530 and the tube capture surface 528 provides for a sharp discontinuity between the various possibilities for loading scenarios aforementioned.

The vertical tube capture surface 528 additionally works in combination with the angled tube engaging surface 526 and the horizontal tube engaging surface 525 to hold the tube 5 securely against the tube stops 576 and to provide for a deformation of the tube 5 by co-action of the angled surface 526, the horizontal surface 525 and the tube stop 576 to lock the tube securely into the tubeway 8 when the longitudinal tubeway aperture is closed as well as to provide substantially full face engagement of the tube 5 with the associated sensors.

The downstream platen 500, or the corresponding upstream platen 800, are preferably constructed of a molded plastic such as glass filled polyphenylsulfide. The downstream platen 500 serves a variety of functions.

The tubeloader bearing cup 502 provides for a mounting area for the tubeloader powertram.

Gearbox sidewalls 503A serve to house the tubeloader gearset 560 is which comprises two helical gears 562, 564 in a perpendicular arrangement so as to transfer rotation from a fore and aft mounted tubeloader motor 550 to the transverse tubeloader camshaft 510. The downstream platen 500 gearbox housing further comprehends a camshaft bushing race 566 which serves to support the downstream camshaft bushing 568 in which the camshaft moves. The forward section of the downstream platen 500 comprises the downstream valve anvil 570 as well as the temperature sensors ports 572 and the lower air sensor transducer housing 574. Abaft of these areas are a plurality of tube stops 576 which serve to support the tube 5 rearwardly so as to provide controlled conformation of the tube 5 when in the loaded condition.

Abaft of the tube supports 576, the downstream platen 500 further provides for the downstream sensor pivot slot 578 which, in concert with associated apparatus, serves to correctly locate the downstream sensor array as shall be described. The rear barrier wall 580, cooperative with chassis 14, serves as a fluid barrier between tube 5 and the electrical components behind the rear barrier wall 580. The rear barrier wall 580 is affixed to the chassis 14 by fasteners and additionally serves a fastening point for the downstream tube present sensor switch 346.

Returning to the foreward edge of the downstream platen 500, a plurality of tubeloader pawl nesting slots 582 are seen. These pawl slots 582, in combination with the tubeloader pawls 514 and the chamfered forward edge 584 of the downstream platen 500, serve to promote a correct loading of the tube 5 into the pump 10 by allowing the pawls 514 to lift and push the tube rearwardly against the tube stops 576. Outward of the outermost of the pawl nesting slots 582, a tube retaining detent 584 serves to retain the tube 5 in a position adapted to be captured by the pawls 514 during initial placement of the tube 5 within the tubeway 8 defined by the raised pawls 514 and the downstream platen 500 when the tubeloading assembly is in a state allowing the tube 5 to be loaded.

As aforedescribed, the tubeloader motor 550 drives, by means of a plurality of gears, the tubeloader camshaft 510. The tubeloader motor 550 is a d.c. motor. The tubeloader motor 550 further comprises a speed reduction gearset 534 operative to provide sufficient torque to rotate camshaft 510 against the drag placed thereon by the components in contact therewith and resident on layshaft 512.

The tubeloader motor shaft 536 extends forwardly from the tubeloader motor 550 and passes through the tubeloader motor mount 538 by way of a central aperture 540 therein.

The tubeloader motor shaft 536 has a flat 542 defined therein which is operative to provide a seat for the tubeloader drive gear setscrew 544 which is inserted through a threaded setscrew aperture 546 in the tubeloader drive gear 562 and thereby fix the rotation of the tubeloader drive gear 562 to that of the tubeloader motor shaft 536.

The tubeloader drive gear 536 is a helical cut gear wherein the teeth thereof are about the circumferential periphery thereof. These teeth engage corresponding teeth on the face of the tubeloader camshaft gear 564, thereby allowing perpendicular actuation of the transversely mounted camshaft 510 by the longitudinally mounted tubeloader motor 550.

The tubeloader camshaft gear 564 is releasably engaged with the camshaft 510 by means of a slideable engagement pin 588.

The camshaft clutch pin 588 is cooperative with a clutch slot 590 on the rear or inboard facing face of the camshaft gear 564. The clutchpin 588 resides transversely to the camshaft 510 in a longitudinal clutchpin slot 592 defined through the camshaft 510. A longitudinal actuator pin 594 coaxially emplaced within the camshaft 510 and in endwise contact with the clutchpin 588 serves to selectively insert and allow the withdrawal of the clutch pin 588 from engagement with the clutch slot 590 on camshaft gear 564. A biasing spring 596 is located within the camshaft 510 and in opposition to the longitudinal actuator pin 594. The outboard end 598 of the actuator pin 594 is rounded to allow sliding contact therewith by the associated component.

Handwheel 600 provides a housing for a pivoting clutch tab 602 which comprises on its inboard facing surface a clutch cam 604 which is in sliding engagement with the outboard end 598 of actuator pin 594. The clutch tab 602 is interior to handwheel 600 and is hinged thereto by a clutch tab pivot pin 606. In operation, actuation of the clutch tab 602 by tilting same about clutch tab pivot pin 606 will cause the clutch cam 604 to impinge on and depress the outboard end 598 of the actuator pin 594 causing the actuator pin 594 to move inwardly against clutch biasing spring 596 and moving clutch pin 588 inwardly and out of contact with the clutch slot 590 in camshaft gear 564, thereby allowing the camshaft 510 to be freely rotated manually by means of handwheel 600 without rotating the camshaft gear 564.

The camshaft 510 is one of the three primary datum shafts resident in the pump 10. The camshaft supports two compound cams denoted as the downstream cam 610 and the upstream cam 620.

The downstream and upstream cams 610, 620 comprise, moving outwardly from chassis, a camshaft deadstop 612, 622, a tubeloaded pawl cam 614, 624 which is itself a compound cam, and valve loading cam 618, 628.

The camshaft deadstops 612, 622 work in cooperation with the chassis rotator stops 28, 30 to provide a positive stop for camshaft rotation. Associated electronics sense the stall condition of the tubeloader motor 550 and interrupt power thereto when the camshaft deadstops 612, 622 are in contact with the chassis rotator stops 28, 30 during an initial indexing cycle of the tubeloader assembly, thereafter the tubeloader 550 in combination with the tubeloader encoder 702, 704, 705 will back-count from the rotator stops 28, 30 and under control of associated software interrupt power to the tubeloader motor 550 prior to the deadstops 612, 622 making contact with the chassis rotator stops 28, 30.

Moving outwardly from the camshaft deadstops 612, 622, the tubeloader pawl cams 614, 624 serve to actuate the tubeloader pawls 514. Additionally, each of the tubeloader pawl cams 614, 624 has a locking surface 616, 626 which serves to activate a second, rigidly affixed lifting follower associated with the tubeloader layshaft 512 so as to provide a positive fixation of the associated elements when the layshaft 512 reaches the end of its travel.

Outward of the pawl cams 614, 624 are the valve loading cams 618, 628. These cams serve to lift the valves 412, 414 out of the tubeway 8 during the loading operation. The valve loading cams accomplish this lift in cooperation with the valve loading tangs 440 as aforedescribed.

Outermost on the camshaft 510 reside the sensor arm cams 630, 632. The downstream sensor arm cam 630 comprises a single surface and is operative to raise or lower the downstream sensor arm.

The upstream sensor arm cam 632, however, is a compound cam having a sensor arm actuating surface 634 and, located outwardly therefrom and integral therewith, the slide clamp loader crank 650.

All of the cams associated with camshaft 510 are fastened thereto by helical pins driven transversely through the hubs of the various cams and through the camshaft 510.

The tubeloader layshaft 512 supports all of the loading members associated with placing the tube 5 in the tubeway 8. Additionally, the layshaft serves to pivotally support other elements which are driven at differing rates than the tubeloader pawls 514. Innermost along layshaft 512, wherein innermost defines that area closer to chassis 14, are the upper jaw pawls 652, 654.

The upper jaw pawls are biased in an upward position by means of helical pre-load springs 656 which are wound about layshaft 512 and are hooked to and have one end hooked to the torsion spring stops 45 and 47, associated with the tubeloader layshaft apertures 44, 46. The other end of the preload spring 656 being hooked onto the respective upper jaw carrier 652, 654. Each of the upper jaw carriers 652, 654 further comprises a forwardly extending arm portion 658 which has a downwardly aimed terminus 660. Forwardly extending arm portion 658 is adapted, in combination with upper jaw tie rod 662, to support the upper pump jaw 220.

The downwardly extending termini 60 of the upper jaw carrier 652, 654 further define a distinctive tubeloading tip shape, as mentioned in the description of the tubeloader pawls 514.

Located rearward of the forwardly extending arm portion 658, a spring slot 664 is formed in the upper jaw carrier 652, 654 and is operative to retain the associated torsion springs 656 therein. The upper jaw carrier 652, 654 have further defined a bifurcated central portion 667 which is adapted to retain the upper jaw carrier locking tangs 668 in the interstice of the bifurcated central portion 667 of the associated upper jaw carrier 652, 654.

Extending rearwardly of the central area 667, an upper jaw carrier cam follower arm 670 has defined therein an upper jaw cam follower port 672 which is adapted to receive the upper jaw carrier arm cam followers 674. The upper jaw cam followers 674 are slidingly retained in the upper jaw cam follower ports 672 and are biased against tubeloader pawl cam 614, 624 by preload-spring 675. The purpose behind this being that should a tube 5 be misloaded beneath the upper jaw 220 or pawls 514, a sensor associated with the position of the upper jaw 220 and in combination with a tubeloader encoder 702, 704, 705, associated with the tubeloader motor armature shaft 701, will detect that the upper jaw 220 and layshaft 514 have ceased their motion while the tubeloader motor continues to rotate as the clearance between the upper jaw carrier cam follower arm 670 and the radially extensive seat 676 of the upper jaw cam follower 674 is closed. An electronic detection circuit will record this differential motion and cause the tubeloader motor 550 to reverse its rotation, opening the upper jaw 220 and tubeloader pawls 514 thereby expelling the tube 5.

To assure a final fixed registration of the upper jaw 220 and the other assemblies driven by layshaft 514, the locking follower 668 rides up on the locking surfaces 616, 626 of the tubeloader pawl cam or layshaft drive cam 614, 624, and is adjustably fixed relative to the upper jaw carrier arm 652, 654 by means of adjustment screws 680. The upper jaw carriers are fixed to layshaft 512 by means of spiral pins so as to actuate a co-rotation thereof.

Figure 16:
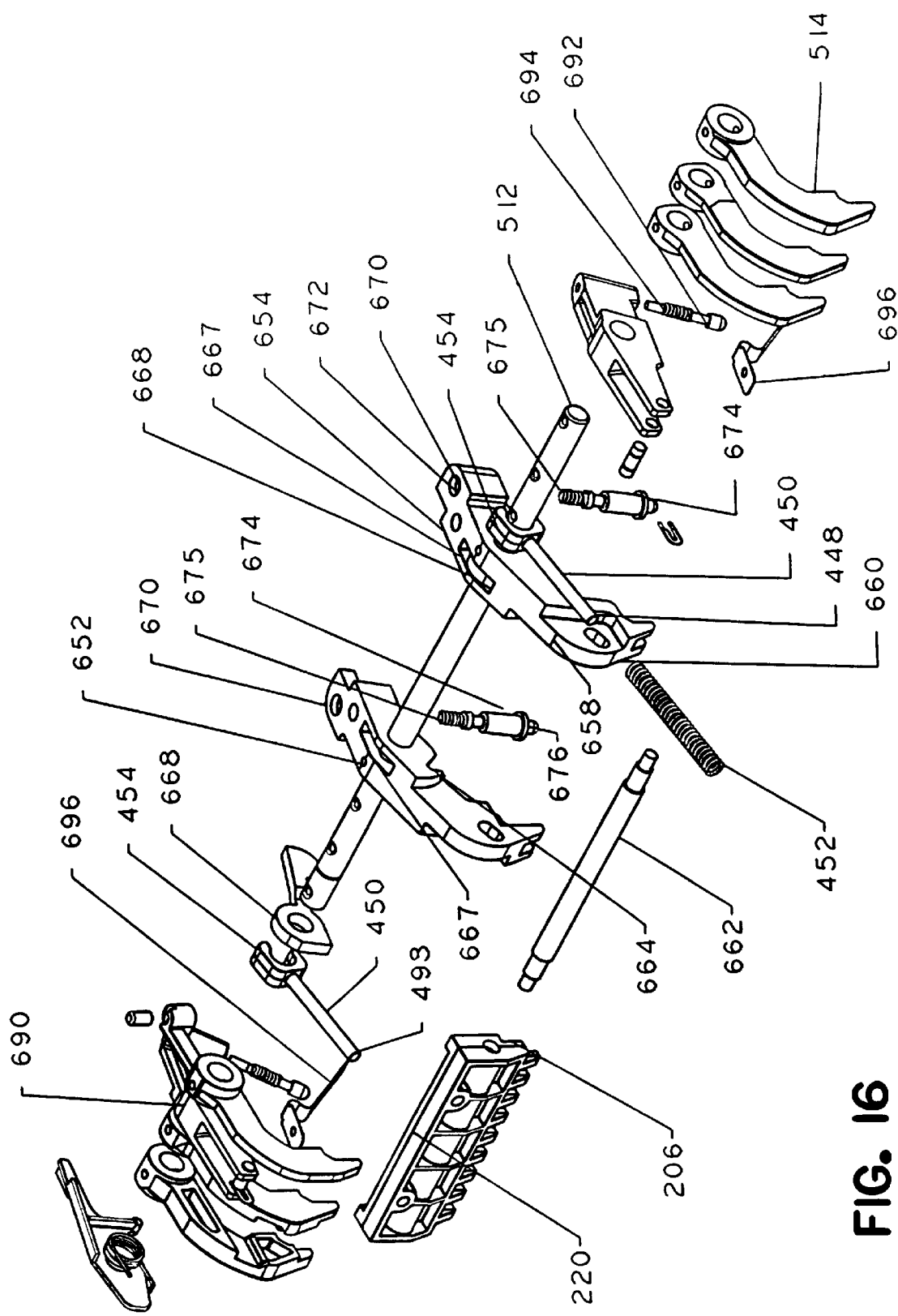
FIG. 16 is an exploded view of the tubeloader sub-assembly.

As seen in FIG. 16, moving outwardly from the upper jaw carrier arms are the valve spring retainers 450. Outward of the valve spring retainers 450 resides the innermost of the tubeloader pawls 514 as aforedescribed.

Associated with, and pivotal about layshaft 512, are the upstream and downstream sensor carrier arms 690. As it is necessary for the tube 5 to be completely loaded in the tubeway 8 before the application of the associated sensors, the sensor carrier arm 690 is actuated by a separate and delayed cam with respect to action of the rest of the components affixed to layshaft 512. Associated with each of the sensor carrying arms 690 is a downwardly extending sensor arm cam follower 692 having a downward biased spring 694 associated therewith. Affixed to a central portion of the sensor carrying arm 690 and in substantially opposing contact with the sensor arm cam 630, 632 is the sensor arm opening spring 696 which, in the preferred embodiment is a leaf spring. This arrangement allows for both the opening of and the closure of the sensor array associated with the upstream or downstream sensor carrier arm 690 by a single cam respectively.

As can be seen in FIG. 16, the sensor arm 690 further comprises a forward forcipate end 698 which is operative in combination with a sensor handle pin 799 inserted thereacross, to support the associated sensor sub-assembly.

Sensors Associated with the Tubeloader Subassembly

Figure 22:
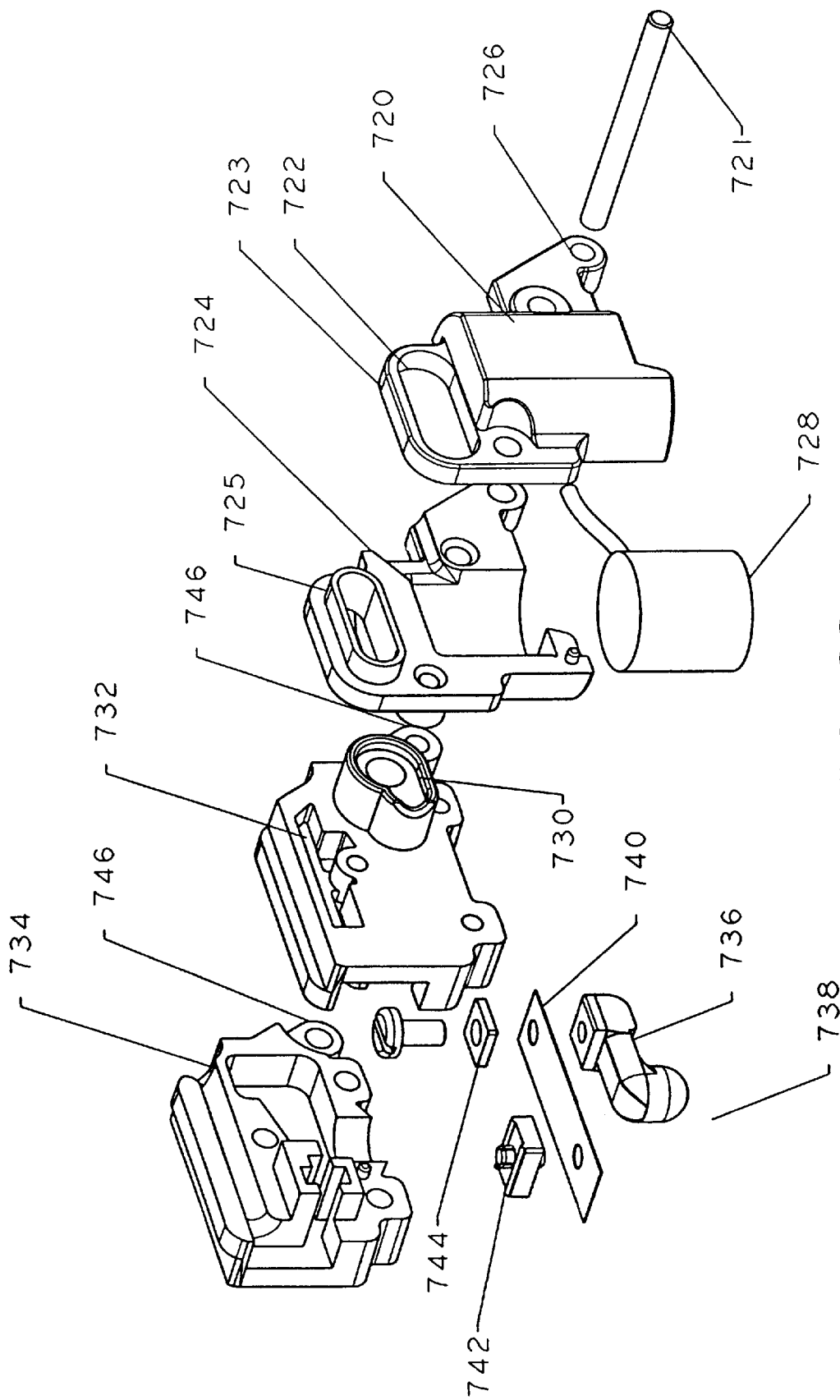
FIG. 22 is an exploded view of the downstream sensor housings.
Figure 23:
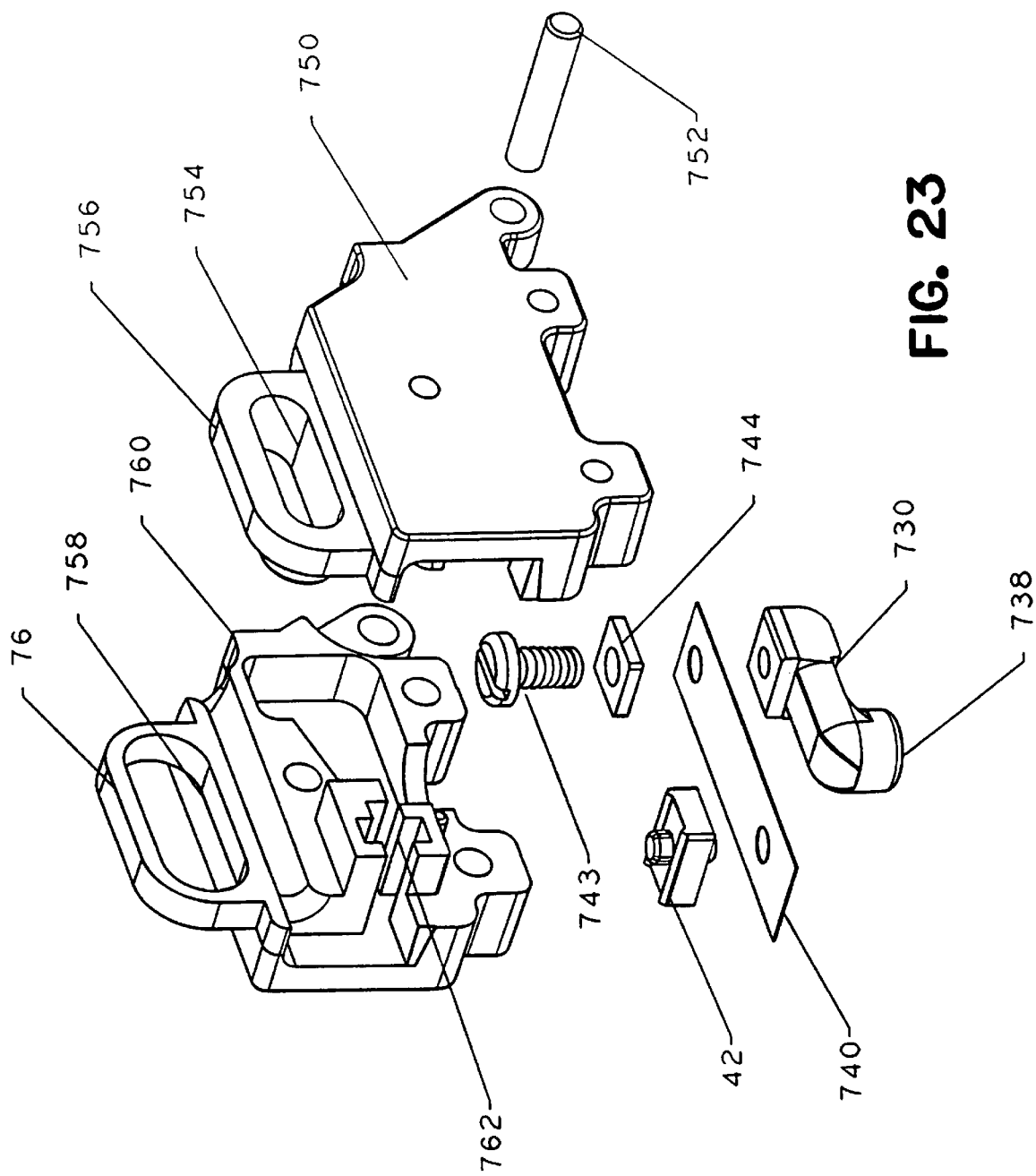
FIG. 23 is an exploded view of the upstream pressure sensor housing.
Figure 24:
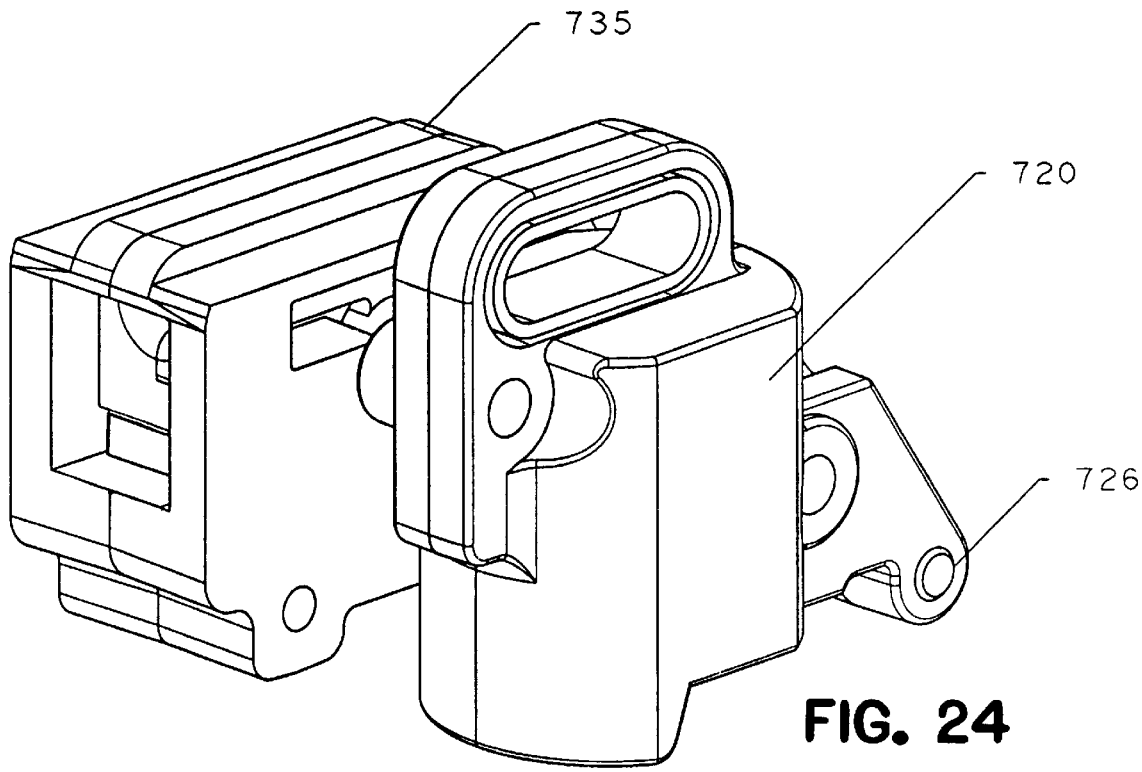
FIG. 24 is an isometric view of the air detector housing as connected to the pressure sensor housing.
Figure 25:
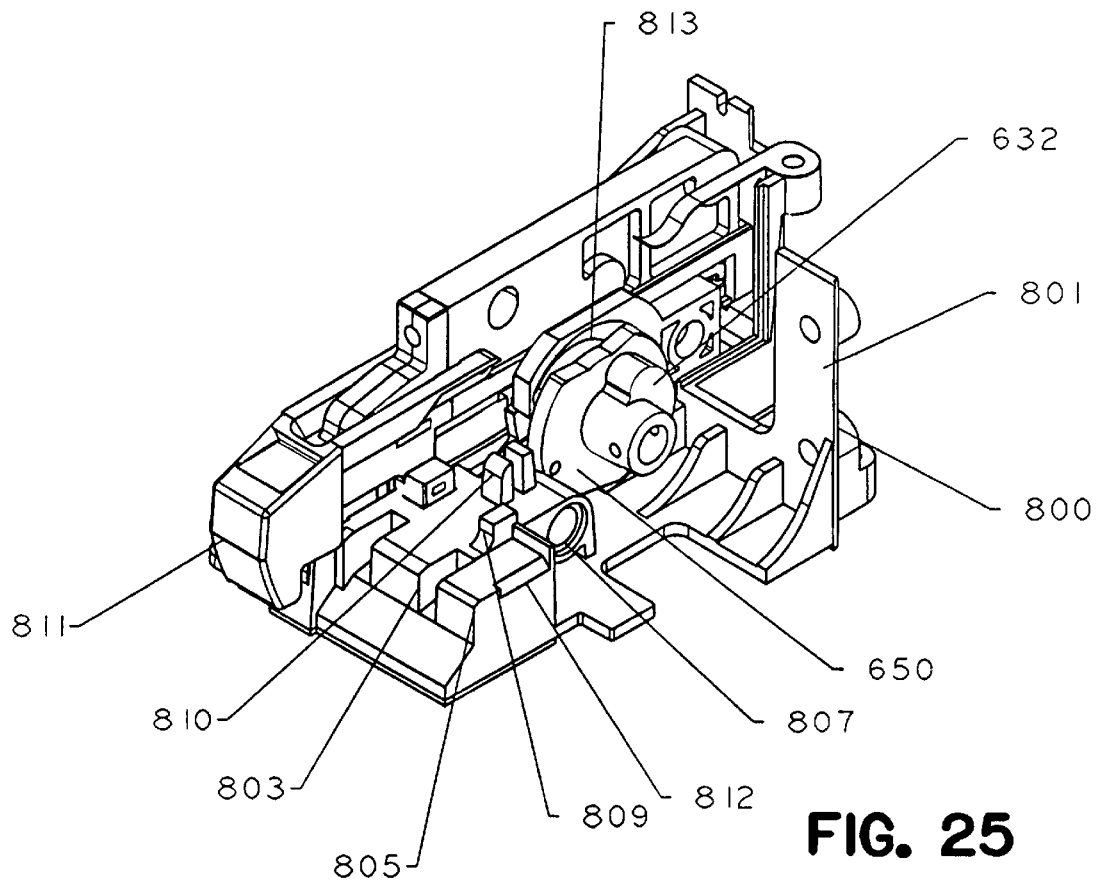
FIG. 25 is an isometric view of the slide clamp loader sub-assembly.
Figure 26:
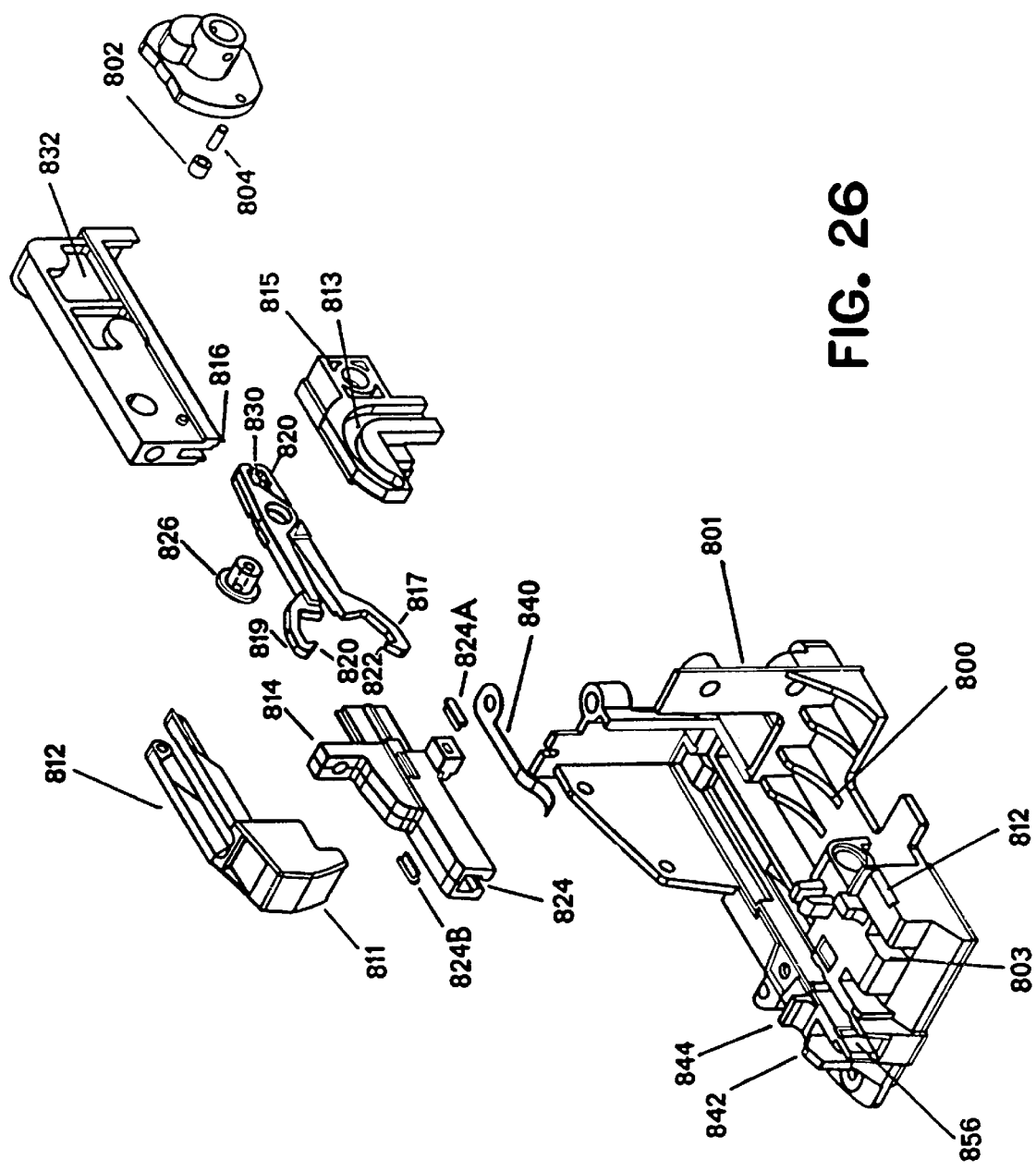
FIG. 26 is an exploded view of the slide clamp loader sub-assembly.
Figure 27:
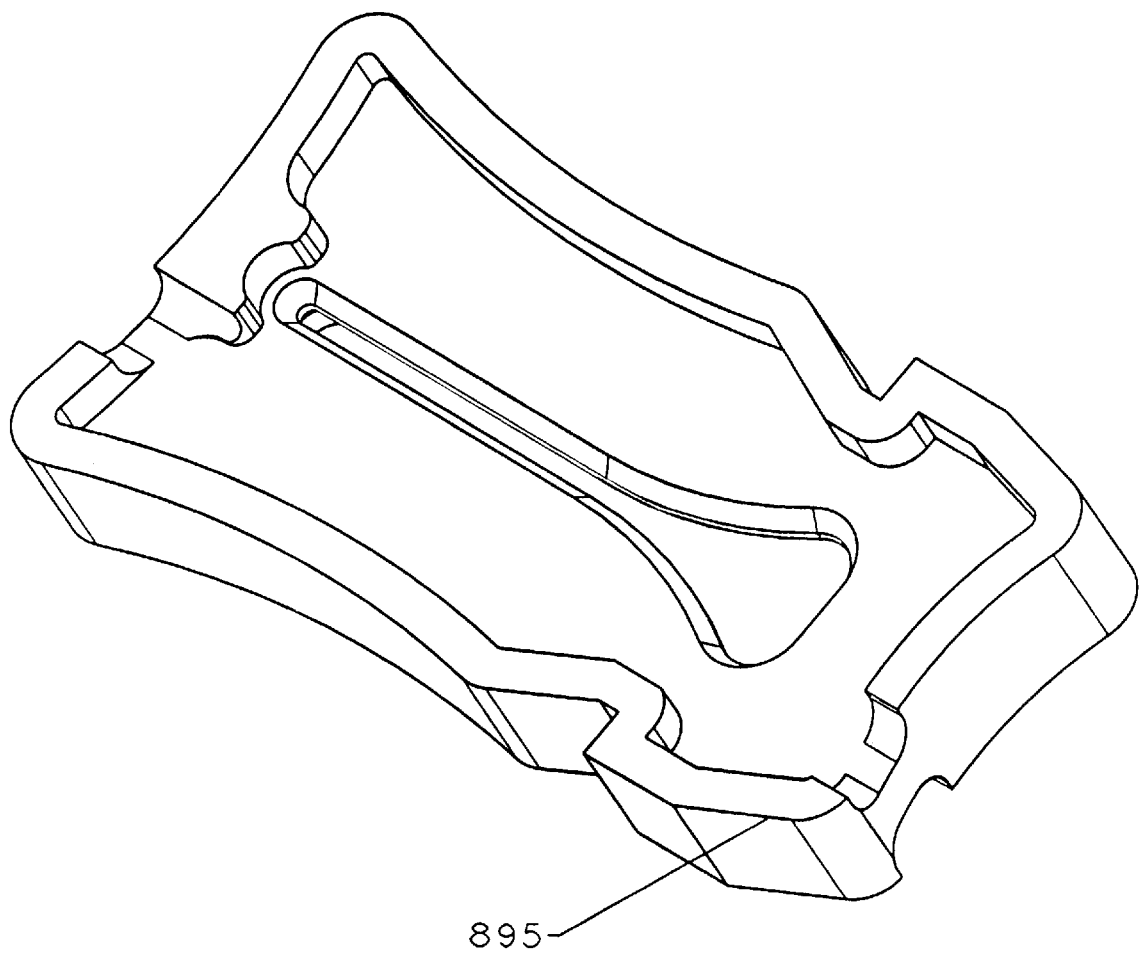
FIG. 27 is an isometric view of the slide clamp.
Figure 28:
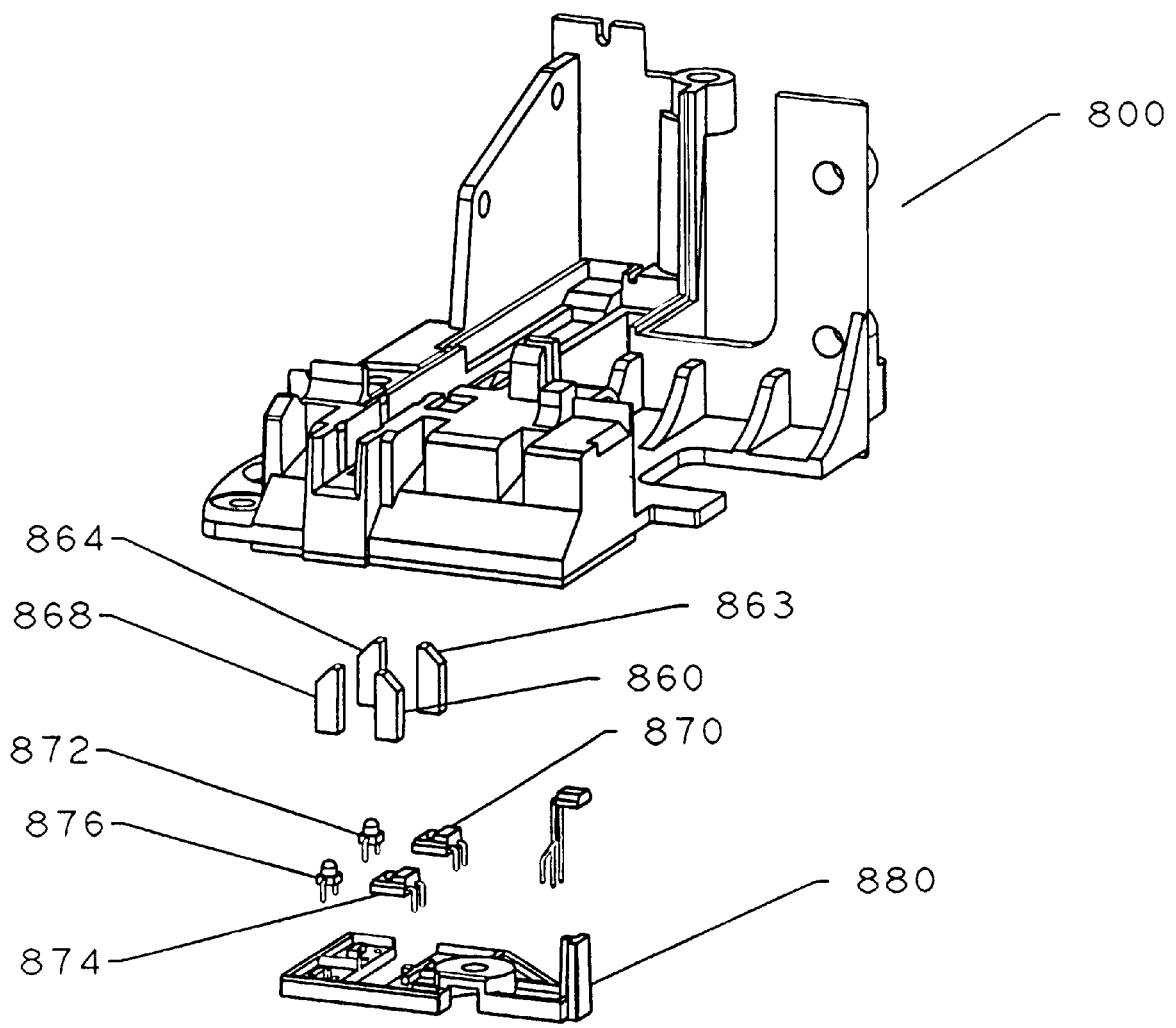
FIG. 28 is an isometric view of the slide clamp sensor and the associated upstream platen.
Figure 29:
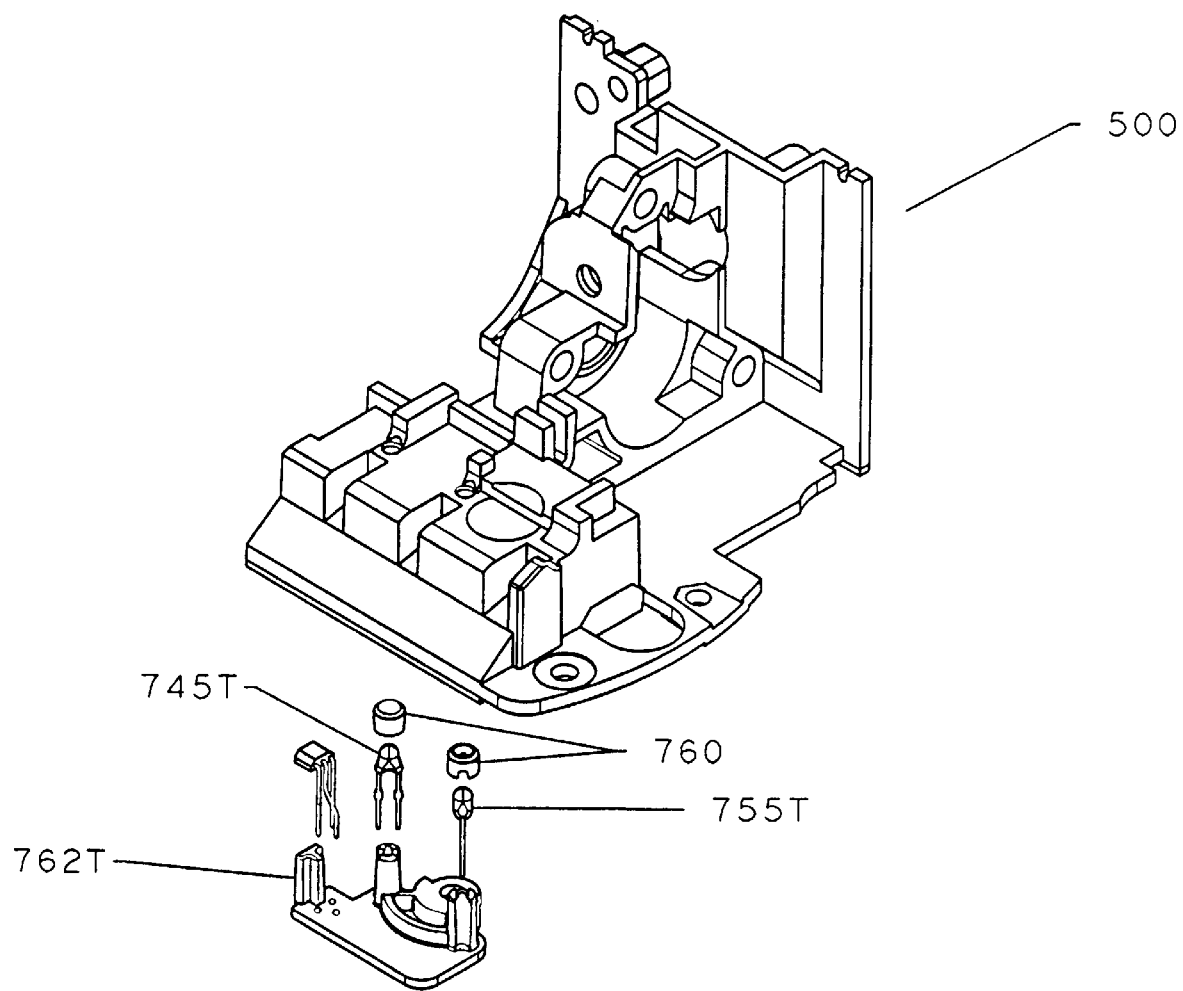
FIG. 29 is an isometric view of the downstream platen with the temperature sensors in an exploded view therebeneath.
Figure 30:
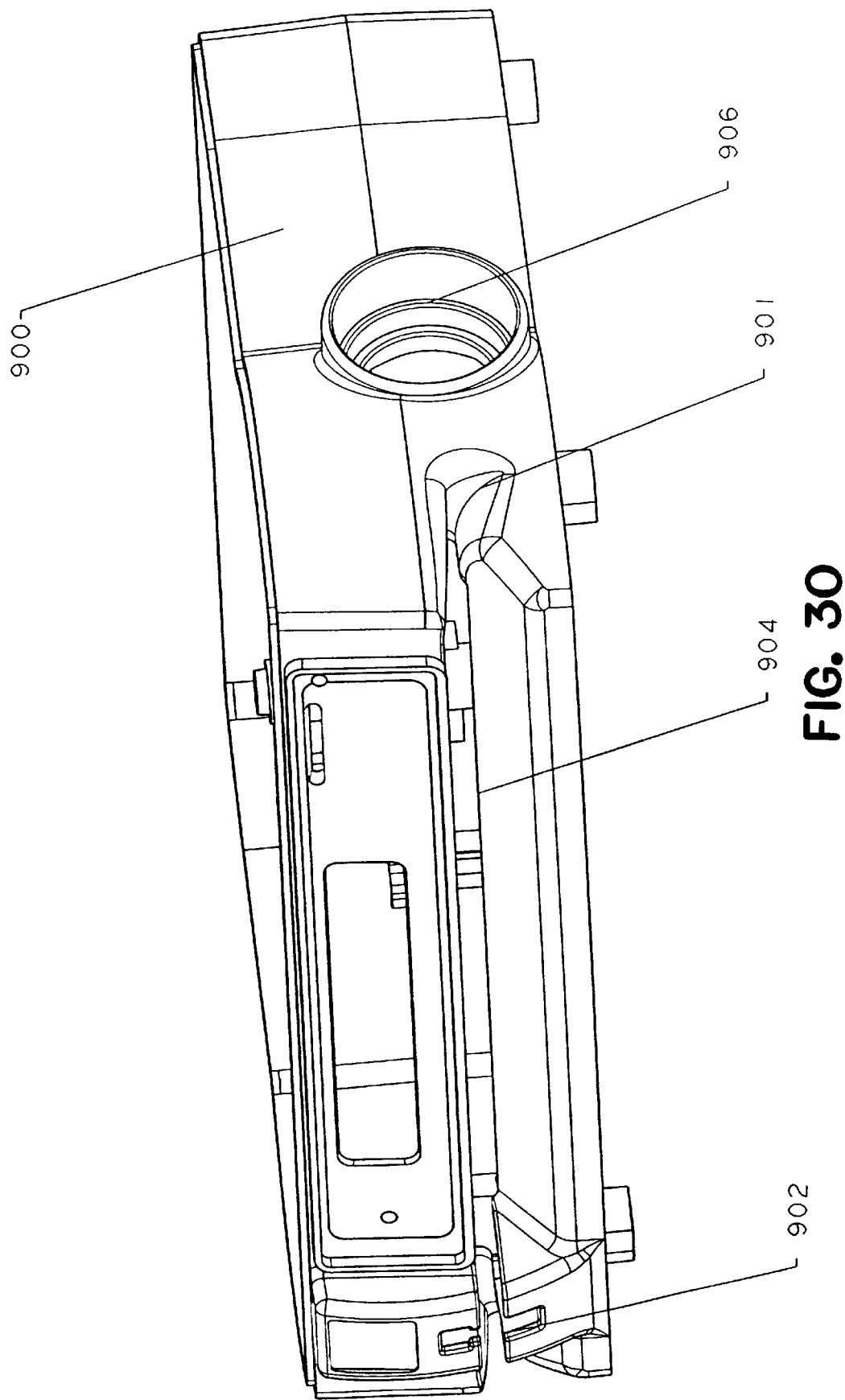
FIG. 30 is an isometric view of the pump housing.

As recited previously, there are a plurality of sensors associated with the sensor arm 690 of the tubeloader subassembly. The most downstream of these sensors is the ultrasonic air detection apparatus or transducer 728 as shown in FIG. 22. The ultrasonic transducer 728 acts in concert with a second transducer element located in the downstream platen 500, as aforedescribed. The ultrasonic transducer 728 is housed in a compoundly pivotal housing 720. This sensor housing 720 comprises a vertically split housing body including a transducer cavity 724. The housing 720 further comprises a substantially horizontally axially extensive suspension slot 722 which, itself, comprehends an oval joining ring 725, which is defined by a substantially oval and longitudinally extensive sensor arm pin retainer 723. The suspension slot 722 serves to capture the sensor handle pin 799, while allowing the sensor assembly 720 to move in fore and aft relation thereto. The sensor assembly 720 is further restrained by the vertically disposed sensor arm pivot slot 578 in combination with sensor housing lift pin 721, which is retained in lift pin ports 726 and 746 allowing vertical axial motion thereof, to allow the sensor 720 to roll over or tilt against the top of tube 5 when the sensor arm cam 630 actuates the substantially downward motion of the forward forcipate end of the sensor arm 690. This ability to roll over, or conversely execute a rocking motion with respect to the tube 5, allows the sensor housing 720 to come into a substantially vertical compressive contact with the tube 5. This allows the tube to be extended or stretched equally across the face of the associated sensor, thereby eliminating either a volumetric or stress gradient in the tube 5 beneath the associated sensor so as to improve the accuracy of response of the sensor associated with, or connected to, housing 720. Essentially all of the sensors associated with, or actuated by, sensor arm 690 execute the above described motion so as to achieve the above described result.

Figure 21:
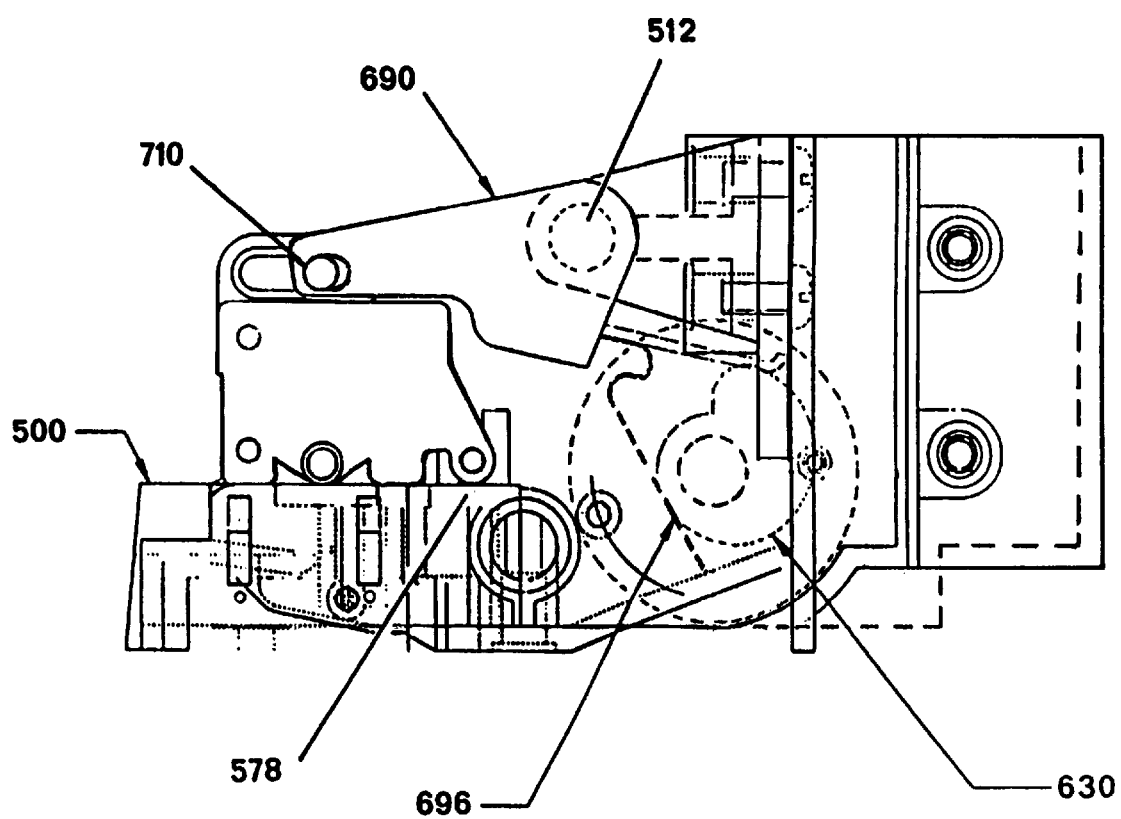
FIG. 21 is a plan view of the sensor housings wherein shadow-views of the open and closed positions thereof are included.

The next sensor located inboardly of the ultrasonic air detection transducer 720 is the downstream pressure sensor which resides in housing 734. The sensor itself comprises a fairly standard, full bridge array on a deflection beam 740. The deflection beam 740 is actuated by a sensing foot 730 which includes a substantially hemispherical tip 738. The hemispherical tip 738 is surrounded by a conical extension of the housing 734. The deflectability of the deflection beam 740 is controlled by seat pin 742 and stiffener 744 in conjunction with sensor foot fastener 743. The hemispherical foot tip 738, in combination with a conical circumferential enclosure thereof has, to achieve maximum accuracy, the requirement that the combination of the foot tip 738 and the conical enclosure be emplaced on the tube 5 in an essentially normal orientation thereto which is achieved by use of a compound rocker arrangement, as previously described, associated with the transducer housing 720 as shown FIG. 21. In this sensor, being contiguous with the ultrasonic detector 720, the compound rocking motion thereof is actuated by the lift pin 721 and oval rocker slot 722 of the transducer housing 720.

The corresponding upstream pressure sensor resident in housing 750, 760 provides an essentially similar layout save that the rocker assembly is unitary with the housing halves 750, 760 and the rocker slot associated herewith is denoted as upstream slot 758 defined in the upstream rocker handle 756 which includes oval inserts 754 and further comprises a separate lift pin 752 riding in an associated vertical slot 810 in the upstream platen 800. Also associated with the tubeloader assembly is the tubeloader motor encoder as aforementioned. The encoder comprises an encoder flag wheel 702 which, in the preferred embodiment, comprehends a tubeloader encoder flag wheel hub 702A and a plurality of flags 702F, resident therebehind is the tubeloader encoder support collar 703 which serves to support the tubeloader encoder optical switches 704, 705 and is affixed to motor 550 via pinch clamp 706 and further supports the optical switch printed circuit board 707.

The downstream platen 500 also serves to support a plurality of temperature sensors which consist of thermistors 754T and 755T which are gasketed to the downstream platen 500 by means of gaskets 760T and are supported from below by the thermistor support 762T.

The Slide Clamp Loader Sub-assembly

The slide clamp loader sub-assembly and its related sensors are generally associated with the upstream platen 800. The upstream platen 800 comprises a rearward facing fluid barrier wall 801 which is connected by fasteners to chassis 14. The fluid barrier wall 801 serves with the rear wall of the chassis and the rear wall of the downstream platen 500 to effectively seal the electronic assemblies from fluid ingress. Mirroring the downstream platen 500, the upstream platen 800 further has defined thereon a tube sweep chamfer 812. With the substantially identical chamfer resident on the shuttle facing interior side of the downstream platen 500, the upstream tube sweep chamfer 812 accounts for forward shift of the tube therefor. The forward facing edge of the upstream platen 800 future defines a plurality of tubeloader pawl nesting slots 803 which are identical functioning to the tubeloader pawl nesting slots 582. Furthermore, the upstream platen further has defined therein a similar forward facing chamfer as the downstream platen chamfer 584.

The upstream platen further has defined thereon the upstream valve anvil 805 and a plurality of tube stops 809 of similar function to the tube stops 576 associated with the downstream platen 500. The upstream platen further receives support from the upstream end of the valve pivot shaft 410 residing in carrier 807. The upstream-most end of the upstream platen 800 further has defined on the exterior peripheral edge thereof a upstream tube retaining detent 842 which is identical in function and cooperative with the corresponding downstream tube retaining detent 584. The base of the upstream platen 800 further has defined thereon a slide clamp loading groove 856. This groove, in combination with the upper slide clamp channel 824 resident in slide clamp carrier 814, serves to capture the slide clamp 895 through which passes tube 5. Additionally, present in the slide clamp channel 824 are a plurality of slide clamp locating pins 824A, 824B which serve to provide, in combination with an asymmetric slide clamp 895, a preferred orientation of the slide clamp 895 and thereby as the slide clamp 895 is already resident on the tube 5, a preferred loading direction of the tube 5 into the pump 10.

The slide clamp loader assembly is driven by camshaft 510 and is actuated by the slide clamp loading crank 650. The slide clamp loading crank 650 has inserted therein a slide clamp loading crank pin 804 upon which rides a slide clamp actuator bushing 802. The rotation of this crank is converted into a substantially linear motion by cooperative movement of the slide clamp actuator bushing 802 and the slide clamp traveler 815 by means of motion of the slide clamp actuator bushing 802 and the slide clamp traveler bushing race 813. The slide clamp traveler 815, in cooperation with the slide clamp clam pin 826, provides substantially fore and aft motion of the slide clamp clams 820, 830, which are operative to grasp and releasably retain the slide clamp 895. The slide clamp clams 820, 830 are in a substantially scissorlike arrangement with respect to each other and reside in the slide clamp clam shell 832, which is operative to allow fore and aft motion of the slide clamp clams 820, 830 therein. The tubeloader pawls further serve to raise the slide clamp shield 811. This ensures that the slide clamp 895 will not be accidentally removed from the pump 10 as the position of the slide clamp traveler 815 provides that shield or visor 811 will be in a lowered position at such time as the pump 10 is in operation, thereby precluding removal of the slide clamp from the slide clamp groove 856.

As aforementioned, slide clamp 895 is adapted to be gripped by the slide clamp clams 820, 830. This is achieved by a cooperation between the slide clamp 895, having detents or grippable elements impressed therein, and the slide clamp loader clam tips 820, 822 which are essentially barblike so as to ensure retention of the slide clamp 895 when the clams are engaged.

In operation the slide clamp loader functions in concert with the tubeloader assembly to ensure correct loading of the tube 5 and the associated slide clamp 895. After the tubeloader pawls 514 close about the tube 5, the slide clamp loading assembly, specifically the slide clamp clams 820, 830, close onto the slide clamp resident about the tube 5 and within the slide clamp groove 856. As the pawls 514 close, and the upper jaw 220 lowers into its operating position, and subsequent to the valves 412, 414 lowering to close off the tube 5, the clams 820, 830 draw the slide clamp 895 into the slide clamp groove 856, thereby opening the slide clamp as it slides past tube 5 which is being retained by the upstream tube stops 844.

The cam arrangement between the valve loading cam races 120, 122 and the tube loader cams assures that the slide clamp will be closed by a reverse of the aforerecited motion of the slide clamp 895 with respect to the tube 5 prior to the tube being in a condition allowing removal thereof from the tubeway 8.

Sensors Associated with the Slide Clamp Loader

The slide clamp loader has two primary sensors associated therewith. The first of these sensors is resident in the upstream platen 800 about the slide clamp groove 856. This sensor is denoted the slide clamp positioning sensor. The slide clamp positioning sensor is located on sensor base 880. Resident on sensor base 880 are two light emitting diodes 872 and 876 which are positioned in a fore and aft arrangement on a first side of the slide clamp groove 856. Diametrically opposed to the light emitting diodes 872, 876 across the slide clamp groove 856, are a corresponding pair of photocells 870, 874. The photocells 870, 874 are also arranged fore and aft to align with the diodes 872, 876. The diodes 872, 876 emit light into a first or transmitting pair of light pipes 864, 868 which extend upwardly above the upstream platen 800 on one side of the slide clamp groove 856. The light pipes 868, 864 terminate in 45 degree internal reflecting surfaces 863 which serve to bend the output of the diodes 872, 876 into horizontal beams transverse to the slide clamp groove 856 at a height suitable for intersection of the beams with a slide clamp 895 present in the groove 856. A corresponding set of receiving light pipes 860, 862 across from the transmitting light pipes 864, 868 serve to receive the light beam emitted by the diodes 872, 876 and transmit same down to the receiving photocells 870, 874 thus putting the light sources and sensors in photonic communication. The receiving light pipes 860, 862 also comprehend 45 degree internal reflecting surfaces 863 in opposing relation to those of transmitting light pipes 864, 868.

In operation the slide clamp sensors serve to identify both the position and presence of a slide clamp 895 in the slide clamp loader sub-assembly. The two sensor sets corresponding to the outer photocell 874 and the inner photocell 870 work in concert to accurately display the location of the slide clamp 895 within the loader sub-assembly. Specifically, the two sensors 874 and 870 determine the location of the slide clamp 895 according to the following truth table wherein high denotes a beam transmitted across the slide clamp groove 856 and low denotes a condition wherein reception of a specific beam is absent.

|                        | Outer Beam | Inner Beam |
|------------------------|------------|------------|
| No Slide Clamp         | High       | High       |
| Clamp Present & Open   | Low        | Low        |
| Clamp Present & Closed | High       | Low        |
| Clamp Not Fully Home   | Low        | High       |

As can be seen from this table, the duality of the sensor array allows not only a detection of the presence or absence of the slide clamp 895, but also detection of the position thereof within the slide clamp groove 856 and, therefore, as the tube 5 is in a fixed location within the tubeway 8, an indication of tile state of the slide clamp 895, namely opened or closed, is also provided.

Also associated with the slide clamp loader sub-assembly, a micro switch 882 in combination with an actuator 882A, which is operated by crank pin 804, serves to detect operation of the tubeloader camshaft 510 by is means of handwheel 600 and with associated electronics will register an alarm when handwheel 600 is rotated.

The Pump Housing

The last of the major sub-assemblies associated with the pump 10 is the pump housing 900. In general aspect, the housing 900, as well as the pump assembly 10, is adapted to be stackable vertically so as to allow, in an alternative embodiment, a plurality of pumps 10 to be driven off of a single associated control module.

The pump housing 900 provides for an attachment and fixation point for the motor mount strap 955 which serves to support the pump motor 24 and the tubeloader motor 550, which are supported in resilient grommets 960, 965, which have associated therewith rotation-suppressing indents 970, 972 which serve to hold securely the two motors 24, 550 and suppress torsional vibration thereof with the co-action of the indents 970, 972 and the corresponding indent-engaging keys 972A, 972B.

The case 900 further consists of a tubeway access slot 904 which has an upstream end 902 and a downstream end 901, wherein both the upstream end 902 and the downstream end 901 are geometrically adapted to form drip loops in the tube 5 by means of a downwardly angled orientation of each of the tubeway access slot ends 901, 902. This geometric adaptation of the tubeway slot ends 901, 902 serves to ensure a conformation of the tube 5 which serves to prevent fluid ingress of the pump 10 from leaks associated with fluid delivery components exterior to the pump 10. The housing 900 further has defined therein an access port 906 adapted to receive therein the tubeloader camshaft handwheel 600 so as to provide access thereto by an operator.

Conclusion

This description of the preferred embodiment of the instant invention is indicative of that embodiment presently preferred and should not be deemed to restrict the scope of the instant invention in any way more restrictive than the scope of the Claims appended hereto, and other and equivalent embodiments of the instant invention are to be deemed as expressly included in the claimed elements of the instant invention.

What is claimed is:

1. A pump for pumping fluid through a tube, said pump comprising a tubeway and a tube present sensor having a first sensor arm with a blade operative to engage said tube and an axis about which said first sensor arm is pivotable and a sensor flag associated with said first sensor arm and an optical switch which is actuated by said sensor flag when a tube is in engagement with said sensor arm blade.

2. The invention according to claim 1 and said tubeway comprising an upstream side and a downstream side and a second sensor arm located on said upstream side of said tubeway and said first sensor arm located on said downstream side of said tubeway.

3. The invention according to claim 2 and a means for controlling operation of said pump wherein said first sensor arm and said second sensor arm are adapted to exchange positional information with said means for controlling operation of said pump wherein said positional information is operative to affect operation of said pump.

4. The invention according to claim 3 and said means for controlling operations of said infusion pump comprising associated electronics and an optical sensor associated with each of said sensor arms wherein the output of said associated electronics is operative to affect operation of said pump.

5. The invention according to claim 1 and associated electronics in communication with said optical switch wherein said associated electronics are operative to control action of said pump dependent on said sensor arm detecting the presence of said tube in said tubeway.

* * * * *